United States Patent [19]
Leeker

[11] Patent Number: 5,330,461
[45] Date of Patent: Jul. 19, 1994

[54] ABSORBENT ARTICLE HAVING FOLDED SIDE FLAPS

[75] Inventor: Karen K. Leeker, Cincinnati, Ohio

[73] Assignee: The Procter & Gamble Company, Cincinnati, Ohio

[21] Appl. No.: 995,462

[22] Filed: Dec. 22, 1992

[51] Int. Cl.$^5$ .............................................. A61F 13/15
[52] U.S. Cl. .................. 604/385.2; 604/387; 604/385.1; 604/389; 604/390
[58] Field of Search ............. 604/358, 385.1, 385.2, 604/387, 389–391

[56] References Cited

U.S. PATENT DOCUMENTS

| | | |
|---|---|---|
| D. 327,319 | 6/1992 | Ruffo et al. |
| 3,397,697 | 8/1968 | Richard |
| 3,800,796 | 4/1974 | Jacob ............................ 604/385.2 |
| 3,926,191 | 12/1975 | Tritsch ............................ 604/390 |
| 3,929,134 | 12/1975 | Karami |
| 4,166,464 | 9/1979 | Korpman |
| 4,285,343 | 8/1981 | McNair |
| 4,327,732 | 5/1982 | Thinnes |
| 4,496,359 | 1/1985 | Pigneul |
| 4,556,146 | 12/1985 | Swanson et al. |
| 4,589,876 | 5/1986 | Van Tilburg |
| 4,596,570 | 6/1986 | Jackson et al. |
| 4,597,759 | 7/1986 | Johnson |
| 4,605,404 | 8/1986 | Sneider |
| 4,608,047 | 8/1986 | Mattingly |
| 4,615,696 | 10/1986 | Jackson et al. |
| 4,654,040 | 3/1987 | Luceri |
| 4,687,478 | 8/1987 | Van Tilburg |
| 4,690,680 | 9/1987 | Higgins |
| 4,701,171 | 10/1987 | Boland et al. |
| 4,701,174 | 10/1987 | Johnson |
| 4,701,178 | 10/1987 | Glaug et al. ........................ 604/389 |
| 4,704,114 | 11/1987 | Wilson et al. |

(List continued on next page.)

FOREIGN PATENT DOCUMENTS

| | | |
|---|---|---|
| 76104512 | 8/1987 | China . |
| 79205822 | 4/1989 | China . |
| 79202379 | 5/1989 | China . |
| 0464855A1 | 1/1992 | European Pat. Off. |
| 0471384A1 | 2/1992 | European Pat. Off. |
| 0471385A1 | 2/1992 | European Pat. Off. |
| 0471587A1 | 2/1992 | European Pat. Off. |
| 0472376A1 | 2/1992 | European Pat. Off. |
| 0511905A1 | 11/1992 | European Pat. Off. |
| 1491234 | 4/1969 | Fed. Rep. of Germany . |
| 3319421 | 11/1984 | Fed. Rep. of Germany . |
| 3326026 | 2/1985 | Fed. Rep. of Germany . |
| 127746 | 7/1992 | Japan . |
| WO89/02729 | 4/1989 | PCT Int'l Appl. |
| WO92/17130 | 10/1992 | PCT Int'l Appl. |
| WO92/18080 | 10/1992 | PCT Int'l Appl. |
| 2118021A | 10/1983 | United Kingdom . |
| 2151460 | 7/1985 | United Kingdom . |

Primary Examiner—Randall L. Green
Assistant Examiner—Rob Clarke
Attorney, Agent, or Firm—Jeffrey V. Bamber; Stephen P. Kearney; Steven W. Miller

[57] ABSTRACT

An absorbent article having a main body portion and a pair of flaps joined to the main body portion. The flaps are folded over the garment side of the main body portion such that the flap adhesives and the central pad adhesives can be covered by a single release liner. The flaps may or may not be used while the absorbent article is being used, i.e., the absorbent article may be used by wrapping the flaps around the edges of the crotch region and securing the flap adhesives to the underside of a user's panty; alternatively, the flaps may be left in their folded configuration on the garment side of the main body portion and the flap adhesives may be secured, along with the central pad adhesive, to the inner crotch region of the panty.

17 Claims, 20 Drawing Sheets

U.S. PATENT DOCUMENTS

| | | |
|---|---|---|
| 4,747,846 | 5/1988 | Boland et al. . |
| 4,756,709 | 7/1988 | Stevens . |
| 4,787,896 | 11/1988 | Houghton et al. . |
| 4,790,838 | 12/1988 | Pigneul et al. . |
| 4,795,455 | 3/1989 | Luceri et al. . |
| 4,834,739 | 5/1989 | Linker et al. . |
| 4,857,067 | 8/1989 | Wood et al. . |
| 4,900,319 | 2/1990 | Richwine . |
| 4,900,320 | 2/1990 | McCoy ................................ 604/389 |
| 4,911,701 | 3/1990 | Mavinkurve . |
| 4,917,697 | 4/1990 | Osborn, III et al. . |
| 4,936,839 | 6/1990 | Molee et al. . |
| 4,940,462 | 7/1990 | Salerno . |
| 4,944,735 | 7/1990 | Mokry . |
| 4,985,025 | 1/1991 | Lingertat et al. . |
| 5,080,658 | 1/1992 | Igaue et al. . |
| 5,087,254 | 2/1992 | Davis et al. . |
| 5,125,918 | 6/1992 | Seidy . |
| 5,133,704 | 7/1992 | Wheeler . |
| 5,133,705 | 7/1992 | Nakanishi et al. . |
| 5,135,521 | 8/1992 | Luceri et al. . |
| 5,151,091 | 9/1992 | Glaug et al. . |
| 5,154,715 | 10/1992 | Van Iten . |

ABSORBENT ARTICLE HAVING FOLDED SIDE FLAPS

FIELD OF THE INVENTION

The present invention relates to disposable absorbent articles, such as female sanitary napkins, adult incontinence devices, and the like. Still more particularly, the present invention concerns such disposable absorbent articles having side flaps and flap adhesive for joining the flaps to the underside of a wearer's panty.

BACKGROUND OF THE INVENTION

All manner and variety of absorbent articles configured for the absorption of body fluids such as menses, urine, and feces are, of course, well known. Absorbent articles, particularly sanitary napkins, having wings or flaps are disclosed in the literature and are available in the marketplace.

Generally, absorbent articles having flaps will comprise a central absorbent means which is provided with an adhesive attachment means, or central pad adhesive, for affixing the central absorbent means to the crotch of a wearer's undergarment. The central pad adhesive is generally provided with a release liner to protect the adhesive from dirt, keep the adhesive from drying out and to keep the adhesive from sticking to extraneous surfaces prior to use. The release liner is peeled from the central pad adhesive to expose the adhesive surface which is then applied to the central crotch region of the panties to secure the central absorbent means in place. After being peeled from the central pad adhesive, the release liner is discarded.

Generally, the flaps of such absorbent articles extend laterally from a central absorbent means and are intended to be folded around the edges of the wearer's panties in the crotch region. Thus, the flaps are disposed between the edges of the wearer's panties in the crotch region and the wearer's thighs.

The flaps serve at least two purposes. First, the flaps prevent exudates which otherwise would soil the edges of the wearer's parities from doing such. Second, the flaps help stabilize the napkin from shifting out of place, especially when the flaps are affixed to the underside of the panties.

Sanitary napkins having flaps of various types are disclosed in U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,271, entitled "Sanitary Napkin", which issued to Clark on Apr. 2, 1957, all of which patents are incorporated herein by reference.

Commonly, the flaps are provided with an adhesive attachment means, or flap adhesive, for affixing the flaps to the underside of the wearer's panties. The flap adhesive is generally provided with a release liner to protect the adhesive from contaminants such as dirt, keep the adhesive from drying out and keep the adhesive from sticking to the skin of the wearer and/or extraneous surfaces prior to use. The release liner is peeled from the flap adhesive to expose the adhesive surface which is then applied to the underside of the panties to secure the flap in place. After being peeled from each of the flap adhesives, the release liners are discarded. However, this arrangement requires the use of two hands to remove the release liner from each flap, i.e., the user must hold the flap with one hand and peel the release liner with the other hand. This also requires the user to dispose of three separate release liners which have been removed from the central absorbent means and each of the flaps of the sanitary napkin. Therefore, there is a need for a sanitary napkin having the flaps arranged relative to the central absorbent means such that the flap adhesives and the central pad adhesives can be covered with a single strip of protective release material.

Several concepts have been proposed to provide an absorbent article comprising a single release liner which protects both the central pad adhesive and the flap adhesives. U.S. Pat. No. 4,701,178 entitled "Sanitary Napkin With Flaps", which issued Oct. 20, 1987 to Glaug et al., teaches a double sided release liner. The first side of the release liner covers the central pad adhesive, and the flap are folded over the release liner with the flap adhesives contacting the second side of the release liner. Alternatively, U.S. Pat. No. 5,133,704 entitled "Intermittent Batwing Adhesive System For Sanitary Napkin", which issued Jul. 28, 1992 to Wheeler, teaches a sanitary napkin having bat-wing flaps (i.e., flaps which are wrapped around the edges of the wearer's panty and secured to each other). The body-facing side of at least one of the flaps has a flap adhesive joined thereto, and the garment side of the absorbent element of the sanitary napkin comprises an adhesive joined thereto which is longitudinally aligned colinearly with the flap adhesive. One side of a single strip of release liner covers both the adhesive of the absorbent element and the adhesive of the body side of the flap.

The absorbent articles of the prior art lack the aspects of the present invention whereby a disposable absorbent article comprising flaps, has flap adhesives joined to the garment side of each flap, and each flap is folded such that the central pad adhesive and the flap adhesives can be covered by one side of a single release liner. Additionally, the absorbent article of the present invention may have either bat-wing flaps or conventional flaps, i.e., flaps which are secured to the undergarment of the wearer as opposed to being secured to the other flap.

While flaps greatly improve the effectiveness of a sanitary napkin, the flaps of a sanitary napkin may hinder or impede application of the sanitary napkin to the crotch of the wearer's panty. Currently, each of the flaps of a sanitary napkin have an end, the distal end, which may move freely relative to the sanitary napkin. Once the release paper of the central pad adhesive is removed by the wearer, the distal ends of the flaps may fall between the crotch portion of the wearer's panty and the sanitary napkin and may become adhered to the central pad adhesive. Therefore, there is a need for a sanitary napkin having flaps positioned so that they will not interfere with the application of the sanitary napkin to the panty.

While sanitary napkins having flaps are commonly viewed as providing better protection against soiling as compared to sanitary napkins without flaps, some women still prefer a sanitary napkin without flaps, and some women who generally prefer a sanitary napkin with flaps, occasionally (such as on light flow days) prefer a sanitary napkin without flaps. However, currently available sanitary napkins having flaps will not function properly unless the flaps are used (i.e, are folded down along the edges of the crotch of the wearer's undergarment and affixed to the underside of the undergarment). For example, prior to use the flaps of a sanitary napkin are folded over the garment side of the sanitary napkin or are folded over the body-facing side of the sanitary napkin. Therefore, if the flaps are not used while the sanitary napkin is being used, the flaps will either obstruct the surface intended to receive bodily exudates on the body-facing side of the sanitary napkin, or will obstruct the adhesive or other fastening means positioned on the garment side of the sanitary napkin. Therefore, there is a need for a sanitary napkin having flaps which may or may not be used while the sanitary napkin is being used.

Absorbent articles, such as sanitary napkins, which can be packaged as individual units have proven to be very useful. Individually packaged absorbent articles are shown in the art. U.S. Pat. No. 4,556,146 entitled "Individually Packaged Disposable Absorbent Article", which issued on Dec. 3, 1985 to Swanson et al., discloses a wrapper which overlays one major surface of an absorbent article and forms an individually packaged disposable absorbent article by folding the article and sealing the wrapper. However, when the absorbent article has flaps, the flaps will interfere with the positioning of the wrapper and will generally have to be positioned out of the way of the wrapper such as on the body-facing side of the article. Therefore, there is a need for an improved disposable absorbent article having flaps, which can be easily formed into an individually packaged disposable absorbent article.

Accordingly, it is an object of the present invention to provide an absorbent article, such as a sanitary napkin, having flaps folded such that the flap adhesives and the central pad adhesives can be protected by a single piece of release liner.

It is also an object of the present invention to provide an absorbent article, such as a sanitary napkin, having flaps which are folded and arranged such that the flaps will not interfere with the application of the sanitary napkin to the crotch of the wearer's panty.

It is an additional object of the present invention to provide an absorbent article, such as a sanitary napkin, having optional side flaps, i.e., flaps which are folded and arranged such that the flaps may or may not be used while the absorbent article is being used.

It is also an object of the present invention to provide a disposable absorbent article having folded flaps and a wrapper which overlays one major surface of the article and the folded flaps to form an individually packaged disposable absorbent article.

These and other objects of the present invention will be more readily apparent when considered in reference to the following description and when taken in conjunction with the accompanying drawings.

SUMMARY OF THE INVENTION

In accordance with the present invention, an absorbent article, such as a sanitary napkin, having flaps is provided. The absorbent article is in a folded configuration and has an adhesive side and a non-adhesive side. The absorbent article comprises a main body portion comprising an absorbent assembly and a pair of flaps joined to the main body portion along a line of juncture. A flap adhesive is joined to the garment side of each flap. Each flap is folded such that the face of the flap adhesive of each flap forms at least a portion of the adhesive side of the absorbent article.

DETAILED DESCRIPTION OF PREFERRED EMBODIMENTS

1. Introduction

A. The Absorbent Article In General

Figure 1:
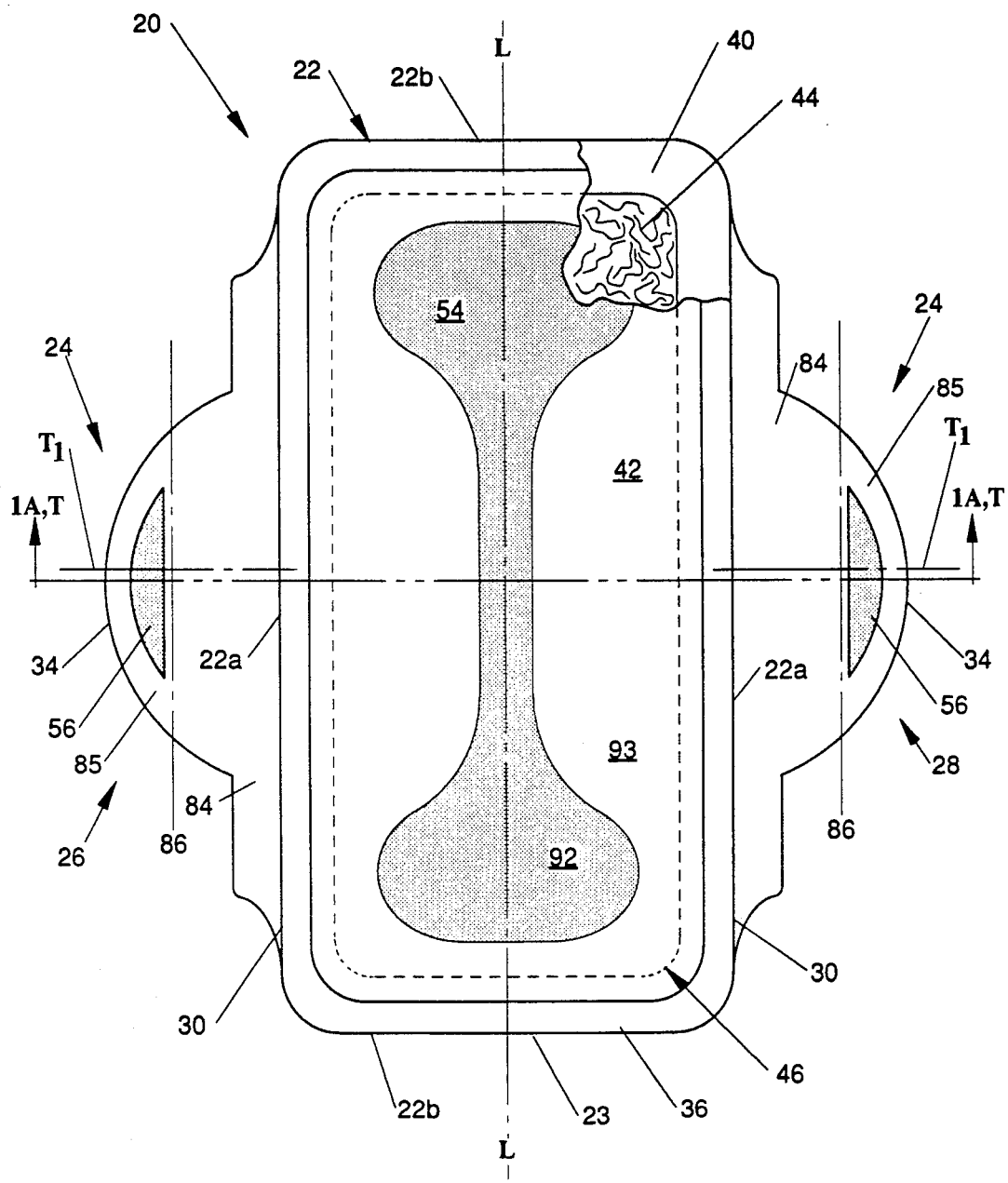
FIG. 1 is a top plan view of a sanitary napkin embodiment of the present invention in a non-folded configuration having portions cut-away to show the absorbent core.

The present invention relates to disposable absorbent articles, such as female sanitary napkins. More particularly, the present invention relates to such disposable absorbent articles having flaps with a flap adhesive which secures the flap to the underside of a user's panty.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include sanitary napkins, pantiliners, and incontinent pads (and other articles worn in the crotch region of a garment). The term "disposable" refers to articles which are intended to be discarded after a single use and preferably recycled, composted, or otherwise disposed of in an environmentally compatible manner. (That is, they are not intended to be laundered or otherwise restored or reused as an absorbent article.)

The term "sanitary napkin", as used herein, refers to an article which is worn by females adjacent to the pudendal region that is intended to absorb and contain the various exudates which are discharged from the body (e.g., blood, menses, and urine). The present invention, however, is not limited to the particular types or configurations of absorbent articles shown in the drawings.

As used herein, the term "optional flaps" refers to a flap or flaps that may or may not be used while the sanitary napkin is being used (i.e., the flaps may be wrapped around the edges of the crotch region and secured to the underside of a wearer's panties or may remain folded over the garment side of the main body portion, without adversely effecting the functionality of the sanitary napkin.

As used herein, the terms "release liner", "release material" or "release member" refer to any material which can be used to protect adhesives, such as the flap adhesives, from dirt, drying out, and/or from sticking to extraneous surfaces prior to use.

As used herein, the term "joined" encompasses configurations whereby an element is directly secured to the other element by affixing the element directly to the other element; configurations whereby the element is indirectly secured to the other element by affixing the element to intermediate member(s) which in turn are affixed to the other element; and configurations whereby one element is integral with another element, i.e., one element is essentially part of the other element.

When the absorbent article of the present invention is said to be "in a folded configuration", this means that the flaps of the absorbent article are folded over the garment side of the main body portion 22. When the absorbent article is in a folded configuration, the absorbent article will have an adhesive side and a non-adhesive side. The non-adhesive side comprises the body facing side of the main body portion. The adhesive side comprises at least a portion of the flap securement member of each flap. The adhesive side may also comprise portions of the garment side of the main body portion and portions of the pad securement member.

A preferred embodiment of the absorbent article of the present invention, sanitary napkin 20, is shown in FIG. 1. The sanitary napkin 20 of FIG. 1 is not in a folded configuration so that the various elements of the sanitary napkin can be clearly shown and described. As shown in FIG. 1, the sanitary napkin 20 basically comprises a main body portion 22 having longitudinal edges 22a, and transverse edges 22b; and two flaps 24 (shown in the extended position) joined to the main body portion 22. Each flap 24 comprises a securement member joined thereto. The main body portion 22 comprises an absorbent means (represented by an absorbent assembly 46) and a central pad securement member (or simply "pad securement member"). (In the discussion that follows, unless otherwise noted, the sanitary napkin described herein will have two flaps. While it is not necessary that the napkin have two flaps, two flaps are preferred over one flap. Also, while it is not necessary that the flaps be mirror images of one another, they preferably are. Thus, the description of one flap will be a description of the other, and, for clarity, discussion of the second flap may be omitted.)

The sanitary napkin 20 has two centerlines, a principal longitudinal centerline L and a principal transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

Figure 1A:
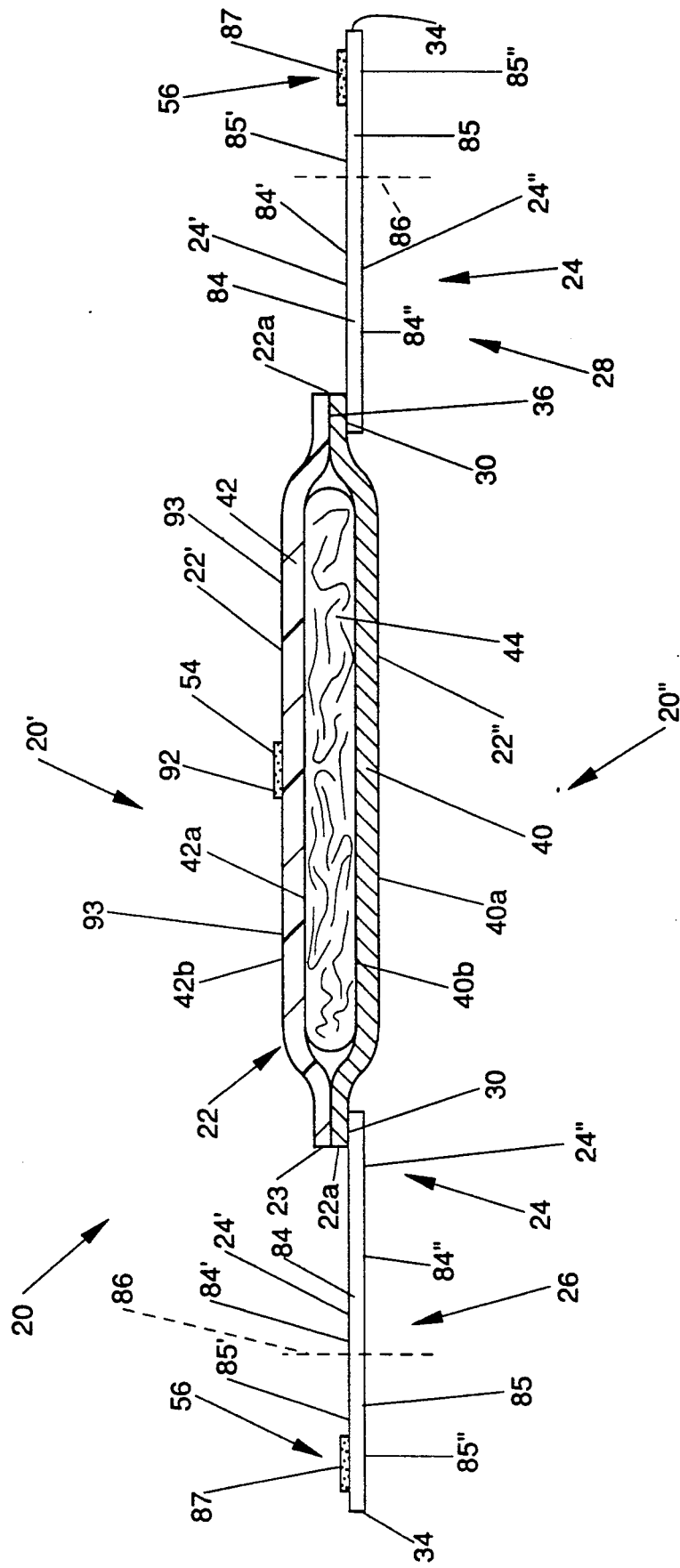
FIG. 1a is a transverse cross-sectional view of the sanitary napkin of FIG. 1 taken along section line 1A—1A.

The sanitary napkin 20 is comprised of a topsheet 40, a backsheet 42, an absorbent core 44, and a pair of flaps 24. At least a part of the topsheet 40, backsheet 42, and absorbent core 44 comprise the absorbent assembly 46 of the main body portion 22. The flaps 24 shown in FIGS. 1 and 1a are comprised of discrete pieces of material which are affixed to the main body portion 22. (In alternative embodiments, such as those shown in U.S. Pat. No. 4,917,697 issued to Osborn, the flaps 24 may be integral with the main body portion 22. In such a case, the topsheet 40 may form one surface of both the flaps 24 and the main body portion 22, and the backsheet 42 may form the other surface of the same. In addition, the absorbent material of the sanitary napkin 20 may extend into the flaps 24 to form a flap absorbent core, as described in greater detail in U.S. Pat. No. 4,917,697. However, for clarity, the flaps of the sanitary napkin will be described as being comprised of discrete pieces of material which are affixed to the main body portion 22.) In a particularly preferred embodiment, the flaps 24 will additionally comprise a zone or zones of differential extensibility as will be described in greater detail hereinbelow.

2. The Individual Components of the Absorbent Article

The individual components of the sanitary napkin 20 will first be looked at in greater detail.

A. The Topsheet

The topsheet 40 is liquid permeable and when the sanitary napkin 20 is in use, the topsheet 40 is in close proximity to the skin of the user. The topsheet 40 is compliant, soft feeling, and non-irritating to the user's skin. It can be made from any of the materials conventional for this type of use. Nonlimiting examples of suitable materials that can be used as the topsheet 40 are woven and nonwoven polyester, polypropylene, nylon, and rayon and formed thermoplastic films, with formed films being preferred.

Suitable formed films are described in U.S. Pat. No. 3,929,135, entitled "Absorptive Structure Having Tapered Capillaries", which issued to Thompson on Dec. 30, 1975, U.S. Pat. No. 4,324,426, entitled "Disposable Absorbent Article Having A Stain-Resistant Topsheet", which issued to Mullane and Smith on Apr. 13, 1982, U.S. Pat. No. 4,342,314, entitled "Resilient Plastic Web Exhibiting Fiber-Like Properties", which issued to Radel and Thompson on Aug. 3, 1982, and U.S. Pat. No. 4,463,045, entitled "Macroscopically Expanded Three-Dimensional Plastic Web Exhibiting Non-Glossy Visible Surface and Cloth-Like Tactile Impression", which issued to Ahr, Louis, Mullane, and Ouellette on Jul. 31, 1984. Formed films are preferred for the topsheet 40 because they are pervious to liquids and yet non-absorbent. Thus, the surface of the formed film which is in contact with the body remains dry and is more comfortable to the wearer.

The sanitary napkin 20. may also be comprised of components that are extensible (i.e., capable of stretching, particularly in the longitudinal direction) when the sanitary napkin is worn. The sanitary napkin 20 may capable of elongating between about 15% and about 40% of its unstretched length. This extensibility provides better in-use fit, comfort, and decreased staining. In other embodiments, only limited portions of the components of the sanitary napkin 20 are capable of stretching. Such an embodiment (without the optional flaps of the present invention) is described in greater detail in co-pending, commonly-assigned U.S. patent application Ser. No. 07/769,891, "Absorbent Article Having Flaps and Zones of Differential Extensibility", filed Oct. 1, 1991, in the name of Bruce Lavash, et al.

A particularly preferred topsheet 40 for use in such an embodiment is one which is made in accordance with U.S. Pat. No. 4,463,045 and ring rolled to provide it with a degree of longitudinal extensibility. Suitable processes for ring rolling or "pre-corrugating" are described in U.S. Pat. No. 4,107,364 issued to Sisson on Aug. 15, 1978, U.S. Pat. No. 4,834,741 issued to Sabee on May 30, 1989 and in co-pending, commonly assigned U.S. patent application Ser. No. 07/662,536 entitled "Improved Method And Apparatus For Incrementally Stretching A Zero Strain Stretch Laminate Web To Impart Elasticity Thereto" filed by Gerald M. Weber et al. on Feb. 28, 1991, U.S. patent application Ser. No. 07/662,537 entitled "Improved Method and Apparatus For Incrementally Stretching Zero Strain Stretch Laminate Web In A Non-Uniform Manner To Impart A Varying Degree of Elasticity Thereto" filed by Kenneth B. Buell et al. on Feb. 28, 1991, and U.S. patent application Ser. No. 07/662,543 entitled "Improved Method And Apparatus For Sequentially Stretching Zero Strain Stretch Laminate Web To Impart Elasticity Thereto Without Rupturing The Web" filed by Gerald M. Weber et al. on Feb. 28, 1991. The fold lines in the corrugations of the topsheet should run in the transverse direction so the topsheet is longitudinally extensible.

Such a topsheet is described in greater detail in the following patent applications which were filed on Jun. 23, 1991: U.S. patent application Ser. No. 07/734,404 entitled "Absorbent Articles, Especially Catamenials, Having Improved Fluid Directionality, Comfort and Fit" filed in the names of Thompson, et al.; U.S. patent application Ser. No. 07/734,392 entitled "Fluid Handling Structure for Use in Absorbent Articles" filed in the names of Thompson, et al.; and, U.S. patent application Ser. No. 07/734,405 entitled "Absorbent Core for Use in Catamenial Products" filed in the names of Buenger, et al. These patent applications may be referred to collectively as the "Capillary Channel Fiber" patent applications.

In addition, in preferred embodiments of the present invention, at least a portion of the outer surface 40a of the topsheet 40 is treated with a surfactant. It is preferred that the surfactant be substantially evenly and completely distributed across at least the portion of the outer surface 40a of topsheet 40 that overlays the main body portion 22. This can be accomplished by any of the common techniques well known to those skilled in the art. For example, the surfactant can be applied to topsheet 40 by spraying, by padding, or by the use of transfer rolls.

Treating the outer surface 40a of the topsheet 40 with a surfactant renders the surface of the topsheet 40 more hydrophilic. This results in liquid penetrating the topsheet 40 faster than it would if the surface were not treated. This diminishes the likelihood that menstrual fluids will flow off topsheet 40 rather than being absorbed by the absorbent core 44. Preferably, any portions of the topsheet 40 that overlay the flaps 24 are not treated with the surfactant. This will minimize any tendencies fluids may have to spread laterally across the flaps and to come in contact with the wearer's thighs and other parts of the wearer's body.

In preferred embodiments, the inner surface 40b of the topsheet 40 is secured in contacting relation with the absorbent core 44. This contacting relationship results in liquid penetrating the topsheet 40 faster than if the topsheet 40 were not in contact with the absorbent core 44. The topsheet 40 can be maintained in contact with the absorbent core 44 by applying adhesive to the inner surface 40b of the topsheet 40. Suitable adhesives useful for this purpose are described in U.S. Pat. No. 4,917,697. The adhesives can be applied by the same methods as the surfactant is applied to the outer surface 40a of the topsheet 40.

B. The Absorbent Core

The absorbent core 44 is positioned between the topsheet 40 and the backsheet 42. The absorbent core 44 provides the means for absorbing menstrual fluid. The absorbent core 44 need not have an absorbent capacity much greater than the total amount of menstrual fluid anticipated to be absorbed. The absorbent core 44 is generally compressible, conformable, and non-irritating to the user's skin. It can comprise any material used in the art for such purpose. Examples include comminuted wood pulp which is generally referred to as airfelt, creped cellulose wadding, absorbent foams, absorbent sponges, synthetic staple fibers, polymeric fibers, hydrogel-forming polymer gelling agents, peat moss, or any equivalent material or combinations of materials.

Polymeric gelling agents are those materials which, upon contact with fluids (i.e., liquids) such as water or body fluids, imbibe such fluids and thereby form hydrogels. In this manner, fluids discharged into the absorbent core 44 can be acquired and held by the polymeric gelling agent, thereby providing the articles herein with enhanced absorbent capacity and/or improved fluid retention performance.

The polymeric gelling agent which is employed in the absorbent core 44 will generally comprise particles of a substantially water-insoluble, slightly cross-linked, partially neutralized, hydrogel-forming polymer material. The term "particles", as used herein, can refer to particles in any form, such as in the form of pellets, flakes, or fibers. The characteristics of the absorbent core 44 (including, but not limited to the preferred types of polymer materials used therein, and types of methods which can be used for preparing these polymer particles) are described in greater detail in U.S. Pat. No. 5,009,653 issued to Osborn and the patents incorporated by reference in that patent, the disclosures of which are all incorporated by reference herein.

In one preferred embodiment, the absorbent core 44 is a laminate comprised of a layer of superabsorbent polymer material, such as in the form of particles, disposed between two air-laid tissues, first and second tissue layers (or "upper" and "lower" tissue layers). The first and second tissue layers provide containment of the superabsorbent polymer material, improve lateral wicking of the absorbed exudates throughout the absorbent core 44 and provide a degree of absorbency.

A suitable laminate is the superabsorbent laminate WATER-LOCK L-535 available from the Grain Processing Corporation of Muscatine, Iowa (WATER-LOCK registered TM by Grain Processing Corporation). Such superabsorbent laminates are disclosed in U.S. Pat. No. 4,467,012, entitled "Composition For Absorbent Film And Method Of Preparation", which issued to Pedersen et al. on Aug. 21, 1984, and U.S. Pat. No. 4,260,443, entitled "Laminated Absorbent Process", which issued to Lindsay et al. on Apr. 7, 1981.

The absorbent core 44 may be a laminate, as described above, which is slitted or partially slitted for longitudinal extensibility. This slitted or partially slitted core is described in greater detail in the Capillary Channel Fiber patent applications.

C. The Backsheet

The backsheet 42 is impervious to liquids and, thus, prevents menstrual fluid from soiling the clothing of the user. Any material used in the art for such purpose can be utilized herein. Suitable materials include embossed or nonembossed polyethylene films and laminated tissue. A suitable polyethylene film is manufactured by Monsanto Chemical Corporation and marketed in the trade as Film No. 8020.

In one alternative embodiment of the sanitary napkin 20 (typically in which the topsheet 40 overlays only the main body portion 22 and does not extend out to form the top surface of the flaps), the backsheet 42 may be comprised of two layers. In such a case, the backsheet 42 may comprise a first layer of lofted material disposed on the core-facing side 42a of the backsheet. The purpose of the first layer is to provide a comfortable, non-irritating surface against the body of the wearer. The lofted layer may be comprised of any suitable material, such as a nonwoven material. Preferably, the lofted layer comprises a hydrophobic nonwoven material. The second layer may be disposed on the garment side 42b of the backsheet 42, and may comprise a fluid impervious film. A low density polyethylene material about 0.01 to about 0.05 millimeters in thickness, preferably about 0.02 millimeters in thickness, has been found to work well as this second layer. A polyethylene film, such as is sold by the Ethyl Corporation, Visqueen Division, under model XP-39385 has been found particularly well suited for this second layer. The backsheet 42 may also be made of a soft, cloth-like material which is hydrophobic relative to the topsheet 40. A polyester or polyolefinic fiber backsheet 42 has been found to work well. A particularly preferred soft, cloth-like backsheet 42 material is a laminate of a polyester nonwoven material and a film such as described in U.S. Pat. No. 4,476,180 issued to Wnuk on Oct. 9, 1984.

A particularly preferred extensible backsheet 42 is an extended adhesive film Formula #198-338 manufactured by the Findley Adhesives Company of Wauwatosa, Wis. which is described in greater detail in the Capillary Channel Fiber patent applications.

3. Assembly of Components into a Sanitary Napkin and Formation of the Optional Flaps

A. Assembly of Components

As shown in FIGS. 1 and 1a, the topsheet 40 is secured to backsheet 42 along a first seam, such as seam 36. The seam 36 can be formed by any means commonly used in the art for this purpose such as by gluing, crimping, or heat-sealing. The seam 36 is illustrated in FIG. 1 as extending completely around the periphery 23 of the absorbent assembly 46 of the main body portion 22. This is a preferred embodiment for ease of construction. (Other means of uniting the various elements can be used.)

The absorbent assembly 46 is the portion of the main body portion 22 that contains an absorbent means, such as absorbent core 44. The absorbent assembly 46 of the main body portion 22 has a liquid pervious body contacting surface (represented in FIG. 1a by topsheet 40) and an opposed liquid impervious surface (represented in FIG. 1a by backsheet 42). It is to be understood that the embodiment illustrated is only one possible embodiment, albeit a preferred one. Other possible embodiments include one in which an absorbent core 44 is essentially completely wrapped with topsheet before it is placed on a backsheet. The absorbent assembly 46 of the main body portion 22 can also comprise an absorbent core which possesses sufficient integrity to stand alone and is liquid pervious on one surface while the other surface has been treated to render it liquid impervious.

The absorbent assembly 46 of the main body portion 22 may be relatively thick or relatively narrow and thin. A narrow absorbent assembly 46 may be effective because the overall configuration and use of sanitary napkin 20 results in absorbent assembly 46 of the main body portion 22 being maintained in close proximity to the body. Such proximity of the absorbent assembly 46 places it precisely where it should be: very near the body at the vaginal opening. The absorbent assembly 46 of the main body portion 22 can then absorb the vast majority of the menstrual fluid (menses) before it has an opportunity to flow along the sides of the main body portion 22. A thin absorbent assembly may also be desired because it is typically comfortable to the user.

FIGS. 1 and 1a also show the pad securement member, central pad adhesive 54, and the flap securement member, flap adhesive 56, which are adapted to secure the sanitary napkin 20 to the crotch region of an undergarment.

Although the pad securement member is described herein as a central pad adhesive 54 and the flap securement member is described herein as a flap adhesive 56, it should be understood that fastening means other than adhesives can be used as the pad securement member and the flap securement member. Any type of fastener or combination of fasteners used in the art can be used for such a purpose. For example, the sanitary napkin 20 could be secured to the wearer's undergarment by the fastener described in U.S. Pat. No. 4,946,527 entitled "Pressure-Sensitive Adhesive Fastener and Method of Making the Same" issued to Battrell on Aug. 7, 1990. Other examples of fastening means would include mechanical fasteners such as those which are well known in the art. Particularly preferred mechanical fasteners are disclosed in commonly-assigned, co-pending, U.S. patent application Ser. No. 07/718,727, "Screen Printing Method for Manufacturing a Refastenable Mechanical Fastening System and Fastening System Produced Therefrom", filed Jun. 21, 1991, in the name of Dennis A. Thomas and David J. K. Goulait, and commonly-assigned, co-pending, U.S. patent application Ser. No. 07/719,211, "Method for Manufacturing a Refastenable Mechanical Fastening System having azimuthally angled Prongs and Fastening System Produced Therefrom", filed Jun. 21, 1991, in the name of Dennis A. Thomas and David J. K. Goulait, which patent applications are incorporated herein by reference. Particularly preferred mechanical fasteners for use with disposable absorbent articles such as a sanitary napkins, are disclosed in U.S. patent application Ser. No. 07/988,636, entitled "Non-Abrasive Mechanical Fastening System And Process of Manufacture Therefor", filed Dec. 10, 1992 in the names of David J. K. Goulait and Dennis A. Thomas, and U.S. patent application Ser. No. 07/988,541, entitled "Absorbent Article Having An Improved Mechanical Fastening System", filed Dec. 10, 1992 in the name of David J. K. Goulait, Dennis A. Thomas, and Maureen E. Stanley, which patent applications are incorporated herein by reference. For simplicity, however, the pad securement member and the flap securement members will be described in terms of adhesive attachment means, i.e., central pad adhesive 54 and flap adhesive 56.

The central pad adhesive 54 provides an adhesive attachment means for securing main body portion 22 in the crotch portion of a panty. The outer surface of flap 24, adjacent the distal edge 34 of the flap, is preferably coated with a flap adhesive 56. The flap adhesive 56 is used to assist in maintaining the flap 24 in position after it is wrapped around the edge of the crotch portion of the panty as described below. The flaps 24 can be maintained in position by attaching the flaps 24 to the undergarment, or to the opposing flap. Suitable adhesive fasteners are described in greater detail in U.S. Pat. No. 4,917,697.

The adhesive attachment means are preferably covered by removable release liners to protect the adhesives from dirt, to keep the adhesives from drying out, and to keep the adhesives from sticking to extraneous surfaces prior to use. Each adhesive attachment means may be provided with a separate release liner. However, the central pad securement member and each flap securement member is preferably covered by a single release liner as will be described in greater detail hereinbelow. Suitable release liners are described in U.S. Pat. No. 4,917,697.

While a preferred sanitary napkin embodiment of the present invention has been described, numerous other sanitary napkin embodiments having flaps are available and are disclosed in the literature. These could be provided with the folded optional flaps 24 of the present invention. In particular, sanitary napkins having flaps are disclosed in U.S. patent application Ser. No. 07/707,233 entitled "Sanitary Napkin Having Laterally Extensible Means for Attachment to the Undergarment of the Wearer", filed May 21, 1991 in the name of Osborn, et al; U.S. Pat. Nos. 5,009,653 and 4,950,264, both entitled "Thin, Flexible Sanitary Napkin" which issued to Osborn on Apr. 23, 1991 and Aug. 21, 1990, respectively, U.S. Pat. No. 4,940,462, entitled "Sanitary Napkin With Expandable Flaps" which issued to Salerno on Jul. 10, 1990, U.S. Pat. No. 4,917,697 entitled "Sanitary Napkin Having Flaps and Stress Relief Means" which issued to Osborn, III, et al. on Apr. 17, 1990, U.S. Pat. No. 4,911,701, entitled "Sanitary Napkin Having Elastic Shaping Means" which issued to Mavinkurve on Mar. 27, 1990, U.S. Pat. No. 4,900,320, entitled "Sanitary Napkin With Panty Gathering Flaps" which issued to McCoy on Feb. 13, 1990, U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,241, entitled "Sanitary Napkin", which issued to Clark on Apr. 2, 1957.

Suitable absorbent articles in the form of pantiliners are disclosed in U.S. Pat. No. 4,738,676 entitled "Pantiliner" issued to Osborn on Apr. 19, 1988. Suitable absorbent articles, at least some of which are in the form of adult incontinence products, are described in U.S. patent application Ser. No. 07/637,571 entitled "Absorbent Article Having Rapid Acquiring Wrapped Multiple Layer Absorbent Body" filed by Barry R. Feist, et al. on Jan. 3, 1991.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

B. Construction of the Flaps

The characteristics of the flaps 24 will now be looked at in greater detail. The general construction of flaps 24 suitable for use in the present invention is described in greater detail in the patents incorporated by reference herein, such as U.S. Pat. No. 4,917,697 issued to Osborn;

U.S. patent application Ser. No. 07/769,891, "Absorbent Article Having Flaps and Zones of Differential Extensibility", filed Oct. 1, 1991 in the name of Bruce Lavash, et al.; and U.S. patent application Ser. No. 07/832,246, "Absorbent Article Having Inwardly-Folded Pleated Flaps", filed Feb. 7, 1992 in the name of Kaoru Niihara and Thomas W. Osborn, III.

The overall size of the flaps 24 can be readily selected by those skilled in the art. Preferably, the flaps 24 are sized so that the sanitary napkin 20 is from about 4 to about 23 centimeters wide between the distal edges 34 of the flaps at their greatest separation. Preferably each flap 24 is from about 5 to at least about 19 centimeters long in the direction parallel to the principal longitudinal centerline L of the sanitary napkin. However, the flaps 24 may be as small as 0.5 centimeters long in the direction parallel to the principle longitudinal centerline L.

The shape of the flaps 24 can be selected by those skilled in the art. Preferably, not only are the flaps 24 mirror images of each other, the two halves of each flap 26 and 28 are also symmetrical about the flap transverse centerline $T_1$. (It should be understood that the shape and orientation of the flaps described herein are those of a preferred embodiment. They are not mandatory design features.)

Preferably, as in the sanitary napkin 20 illustrated in FIG. 1, the flaps 24 are positioned slightly forward of the principal transverse centerline T of the sanitary napkin. (In such a case, the flap transverse centerline $T_1$ does not coincide with the principal transverse centerline T of the sanitary napkin 20.) The flaps 24, however, are preferably evenly spaced from the principal longitudinal centerline L of the sanitary napkin.

In a preferred embodiment, the flaps 24 are joined with the main body portion 22 along lines of juncture 30. The lines of juncture can be concave, straight, or convex relative to the principal longitudinal centerline L. The lines of juncture 30 may comprise those lines or areas where separate flap elements are joined to the main body portion 24. Alternatively, when the flaps 24 are integral with the main body portion 22, the lines of juncture 30 may represent lines of demarcation between the main body portion 22 and the flaps 24 (although it is not necessary that there be a precise line of demarcation).

The flaps 24 can be joined with the main body portion 22 in a number of different manners. Many of the different ways a component (such as the flaps 24) can be "joined to" or "associated with", etc. another component, are set forth in the definitions of these terms contained in U.S. Pat. No. 5,007,906 entitled "Decoupled Sanitary Napkin" which issued to Osborn, et al. on Apr. 16, 1991. When the flaps comprise separate elements, they can be joined to the main body portion 22 by any techniques known to those skilled in the art. Such techniques include, but are not limited to adhesives, heat and/or pressure, ultrasonics, etc.

It is not necessary that the flaps 24 extend from (or be joined along) the longitudinal edges 22a of the main body portion 22. The flaps 24 can joined inward (or "inboard") from the longitudinal edges 22a toward the longitudinal centerline such as is shown in U.S. Pat. No. 4,900,320 issued to McCoy on Feb. 13, 1990. The flaps 24 can, thus, each be joined to the main body portion 22 along the principal longitudinal centerline L, or along the longitudinal edges 22a of the main body portion 22, or at any place between the principal longitudinal centerline L and the longitudinal edges 22a of the main body portion 22. The flaps 24 will, of course, generally be on opposite sides of the principal longitudinal centerline L.

C. The Optional Flaps

Figure 2:
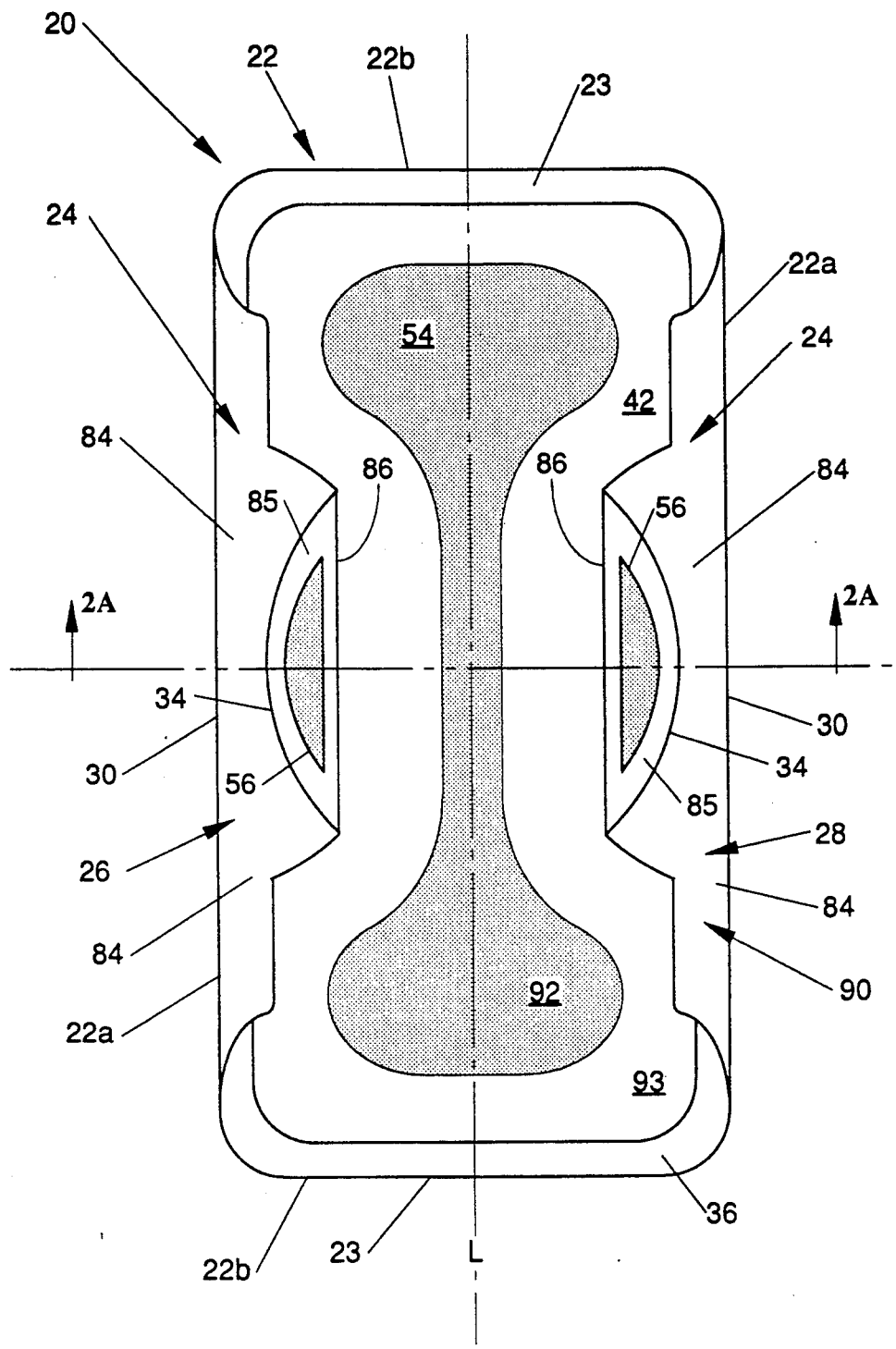
FIG. 2 is a top plan view of the sanitary napkin embodiment of FIG. 1 in the folded configuration of the present invention.
Figure 2A:
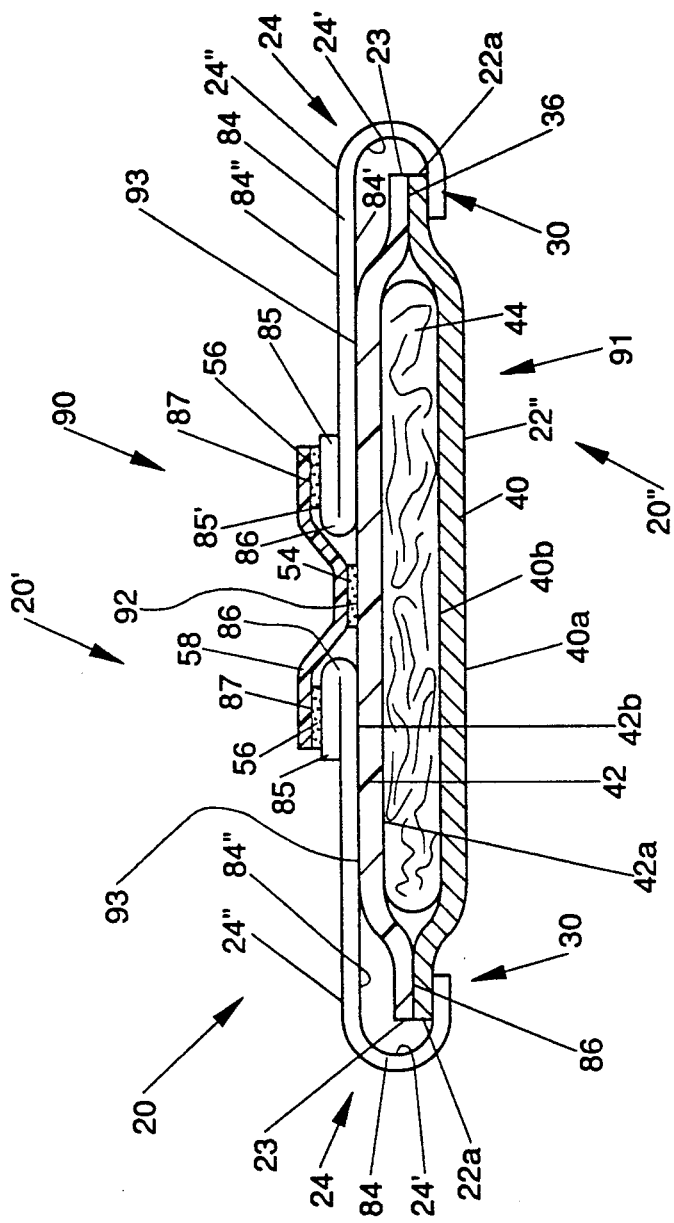
FIG. 2a is a transverse cross-sectional view of the sanitary napkin of FIG. 2 taken along section line 2A—2A.

FIGS. 2 and 2a show a preferred sanitary napkin 20 embodiment of the present invention. The sanitary napkin 20 of FIGS. 2 and 2a are shown in a folded configuration. FIG. 2 is a plan view of the adhesive side 90 of the sanitary napkin 20 in a folded configuration. For clarity, the release liner 58 is not shown in FIG. 2. With the flaps 24 in this folded configuration, the face 87 of the flap adhesive 56 of each flap 24 forms a portion of the adhesive side 90 of the sanitary napkin 20. Accordingly, the sanitary napkin 20 may be used by securing the pad securement member to the crotch of the wearer's panty, wrapping the distal edges 34 of the flaps 24 around the edges of a wearer's panty, and securing the flaps 24 to the underside of the undergarment. Alternatively, the sanitary napkin 20 may be used by leaving the flaps 24 in a folded configuration and securing the flap securement members and the pad securement members to the crotch of the wearer's panty. In either case, the flaps 24 will not adversely effect the functionality of the sanitary napkin 20, i.e., will not adversely effect the ability of the absorbent assembly 46 to absorb bodily fluids.

Referring to FIG. 1, each flap 24 of the sanitary napkin 20 comprises a fold line 86, a first portion 84 inboard of the fold line 86, and a second portion 85 outboard of the fold line 86. As shown in FIG. 1a, each flap 24 comprises a flap adhesive 56 joined to the garment side 85' of the second portion 85. The flap adhesive 56 comprises a face 87 that is oriented away from the garment side 85' of the second portion 85. The face 87 is that portion of the flap adhesive 56 that is generally intended to adhere to a portion of the user's undergarment.

Referring to FIG. 1a, it can be seen that the sanitary napkin 20 has a garment side 20' and a body facing side 20". The garment side 20' of the sanitary napkin 20 is the side generally oriented toward the undergarment when the sanitary napkin is positioned in the crotch region of the undergarment of the wearer. The body facing side 20" of the sanitary napkin 20 is the side generally intended to absorb bodily fluids and is oriented toward the body of the wearer when the sanitary napkin is positioned in the undergarment.

Referring to FIG. 1a, the main body portion 22 has a garment side 22' and a body facing side 22". The flaps 24 also have a garment side 24' and a body facing side 24". The garment side of any element of the sanitary napkin 20 is the side generally oriented toward the undergarment of the wearer when the flaps 24 are wrapped around the edges of the crotch region of the undergarment and secured to the underside of the undergarment. The body facing side of any element of the sanitary napkin 20 is the side opposite the garment side. The garment side of an element is generally denoted by a prime symbol (') following the reference numeral of the particular element. The body-facing side of an element is generally denoted by a double prime symbol (") following the reference numeral of the particular element. Although the sanitary napkin 20 of the present invention can be used without utilizing the flaps 24, i.e., wrapping the flaps around the edge of the crotch region and securing them to the underside of the undergarment, the garment side of each flap 24 is the side of the flap 24 which would be generally oriented toward the undergarment of the wearer if the flap was wrapped around the edges of the crotch region of the undergarment.

Referring to FIG. 2a, the sanitary napkin 20 is in a folded configuration and comprises an adhesive side 90 and a non-adhesive side 91. The non-adhesive side 91 comprises the body facing side 22" of the main body portion 22. The adhesive side 90 comprises the face 87 of the flap adhesives 56, portions of the garment side 22" of the main body portion 22, and the pad securement member, central pad adhesive 56.

Referring to FIG. 2 and 2a, each flap 24 is folded over the garment side 22' of the main body portion 22 such that a portion of the garment side 22' of the main body portion 22 is superposed by the garment side 84' of the first portion 84 of each flap 24. Each of the flaps is also folded along the longitudinally extending fold line 86 such that the body facing side 85" of the second portion 85 superposes a portion of the body facing side 84" of the first portion 84 and the garment side 85' of the second portion 85 with the flap adhesive 56 joined thereto, will be oriented away from the garment side 22" of the main body portion 22. Therefore, when the sanitary napkin 20 is in this folded configuration, the face 87 of the flap adhesives 56 will form a portion of the adhesive side 90 of the sanitary napkin 20. In a preferred embodiment of the present invention, a single release liner 58 will be used to cover and protect both the central pad adhesive 54 and the flap adhesives 56 as shown in FIG. 2a.

Referring to FIGS. 1 and 2, it can be seen that the central pad adhesive 54 is shaped to form securement regions 92 and non-securement regions 93 on the garment side 22' of the main body portion 22. Referring to FIG. 2a, it can be seen that when the flaps 24 are folded over the garment side 22' of the main body portion 22, the flaps superpose the non-securement regions 93 of the main body portion 22. In such an embodiment, the flaps may be held in position by one or more releasable or breakable pinpoint heat seals, adhesive bonds, or the like. The flaps may also be held in position by the structural integrity of the flap 24 itself, i.e., the flap may be capable of maintaining itself in a folded configuration.

Figure 3:
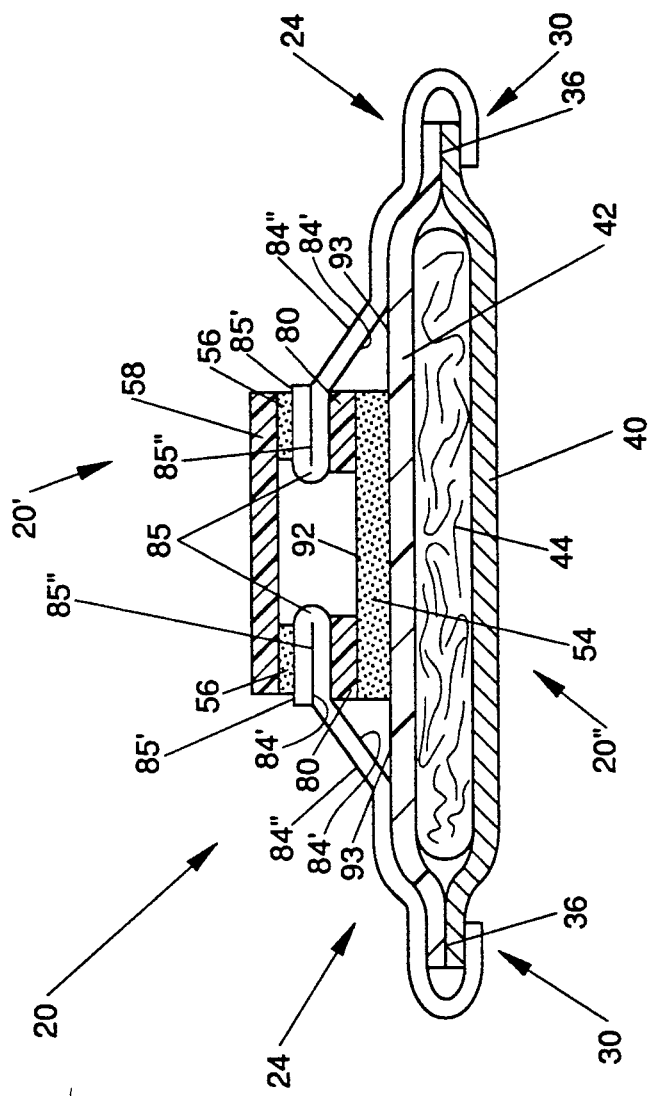
FIG. 3 is a transverse cross-sectional view of an alternate sanitary napkin embodiment of the present invention.

FIG. 3 shows a sanitary napkin embodiment of the present invention wherein the flaps 24 superposes at least a portion of the securement region 92 formed by the central pad adhesive 54 of the main body portion 22. In such an embodiment the securement region 92 will hold the flaps in position on the garment side of the sanitary napkin 20. This can be accomplished by using a central pad adhesive 54 which forms a larger securement region in the area where the flaps will superpose the main body portion 22 such that a portion of each of the flaps 24 superposes a portion of the securement region 92. Alternatively, this may be accomplished by providing the sanitary napkin 20 with flaps 22 which when folded over the garment side 22' of the main body portion 22, are capable of superposing at least a portion of the securement region 92 of the main body portion 22. The sanitary napkin embodiment of FIG. 3 will be described in greater detail hereinbelow.

The sanitary napkin of the present invention can be made by any suitable method. For example, the sanitary napkin of the present invention can be made by assembling the main body portion 22 and flaps 24 as described hereinbefore, applying the flap adhesives 56 to the flaps 24, applying the central pad adhesive 54 to the main body portion 22, and then folding the flaps over the garment side 22' of the main body portion 22 such that the face 87 of the flap adhesive 56 of each flap 24 forms a portion of the adhesive side 90 of the sanitary napkin 20.

The central pad adhesive 54 and the flap adhesive 56 can be applied by any suitable method. Methods of applying adhesives to disposable absorbent articles are well known in the art. Examples of suitable methods of applying adhesives to disposable absorbent articles include spraying, printing (such as by gravure or screen printing), or the like. Preferably, the central pad adhesive 54 and flap adhesives 56 are applied simultaneously. A preferred method of simultaneously applying the central pad adhesive 54 and the flap adhesives 56 is by coating one side of a release liner with a layer of adhesive such as pressure sensitive adhesive and then applying the release liner to the adhesive side 90 of the sanitary napkin 20 such that the pressure sensitive adhesive is transferred simultaneously to the the main body portion 22 and flaps 24. A commercially available release liner having an adhesive joined thereto is manufactured and marketed by 3 Sigma of Covington, Ohio (a division of Anchor Continental of Columbia, S.C.) and is known as "Shield Tape" or "3 Sigma-Shield Tape".

Figure 8:
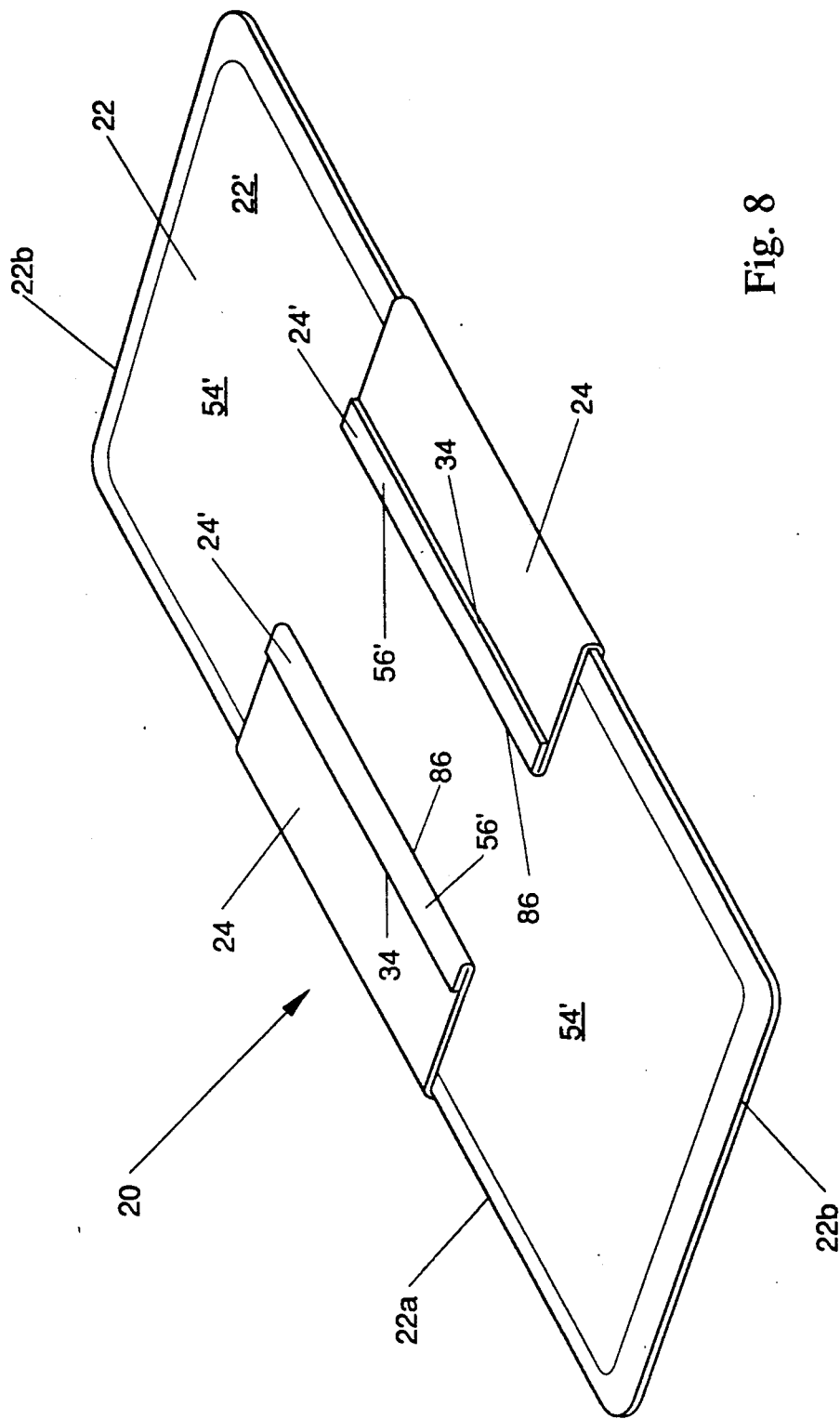
FIG. 8 is a perspective view of a sanitary napkin embodiment of the present invention prior to the adhesive being applied to the adhesive side of the sanitary napkin.
Figure 8A:
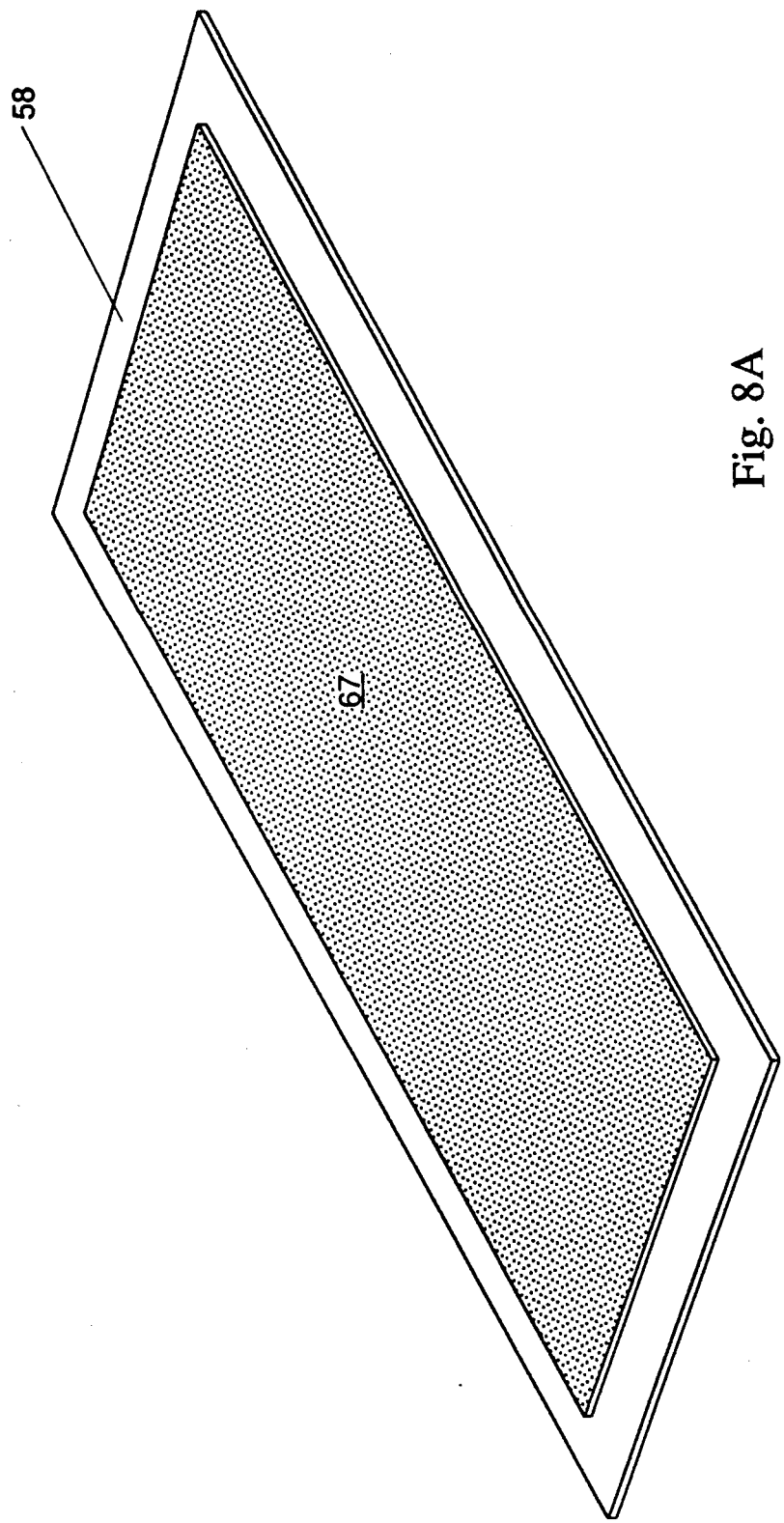
FIG. 8a is a perspective view of a release liner having an adhesive patch removably secured thereto.
Figure 8B:
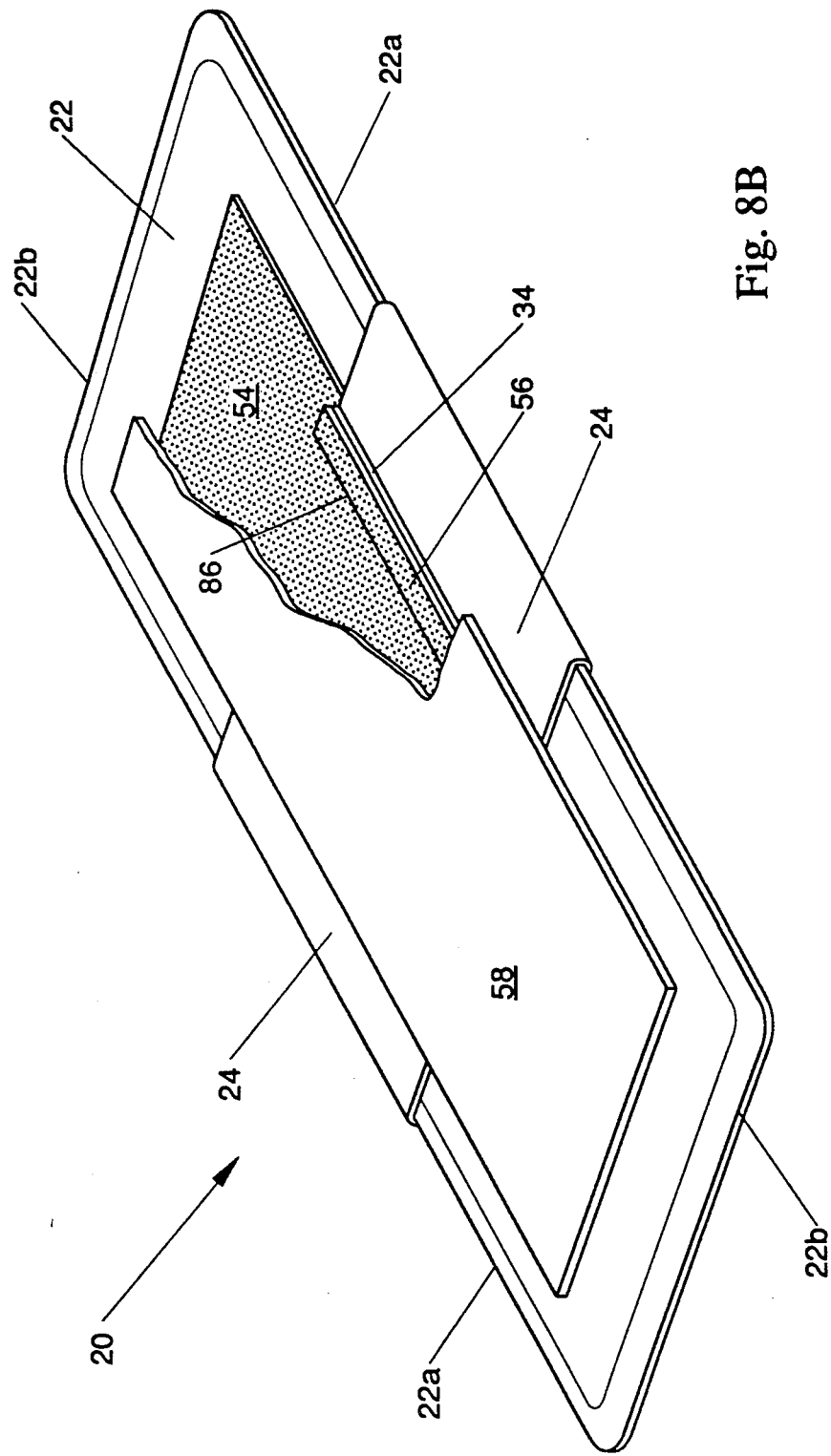
FIG. 8b is a perspective view of the sanitary napkin of FIG. 8 after the release liner and adhesive patch have been applied thereto, the release liner is partially cut-away to show the flap adhesive and the central pad adhesive.
Figure 8C:
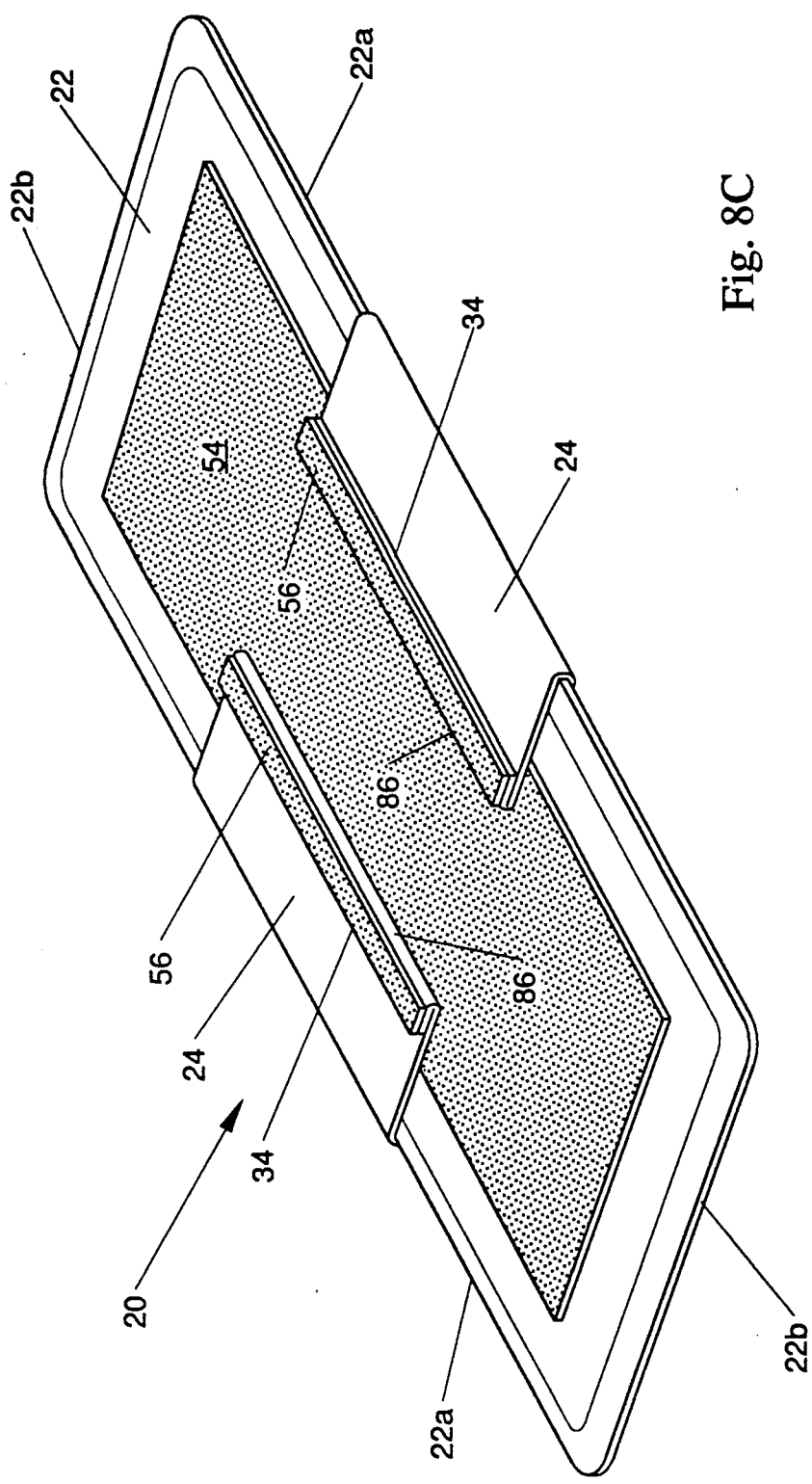
FIG. 8c is a perspective view of the sanitary napkin of FIG. 8b after the release liner has been removed.
Figure 8D:
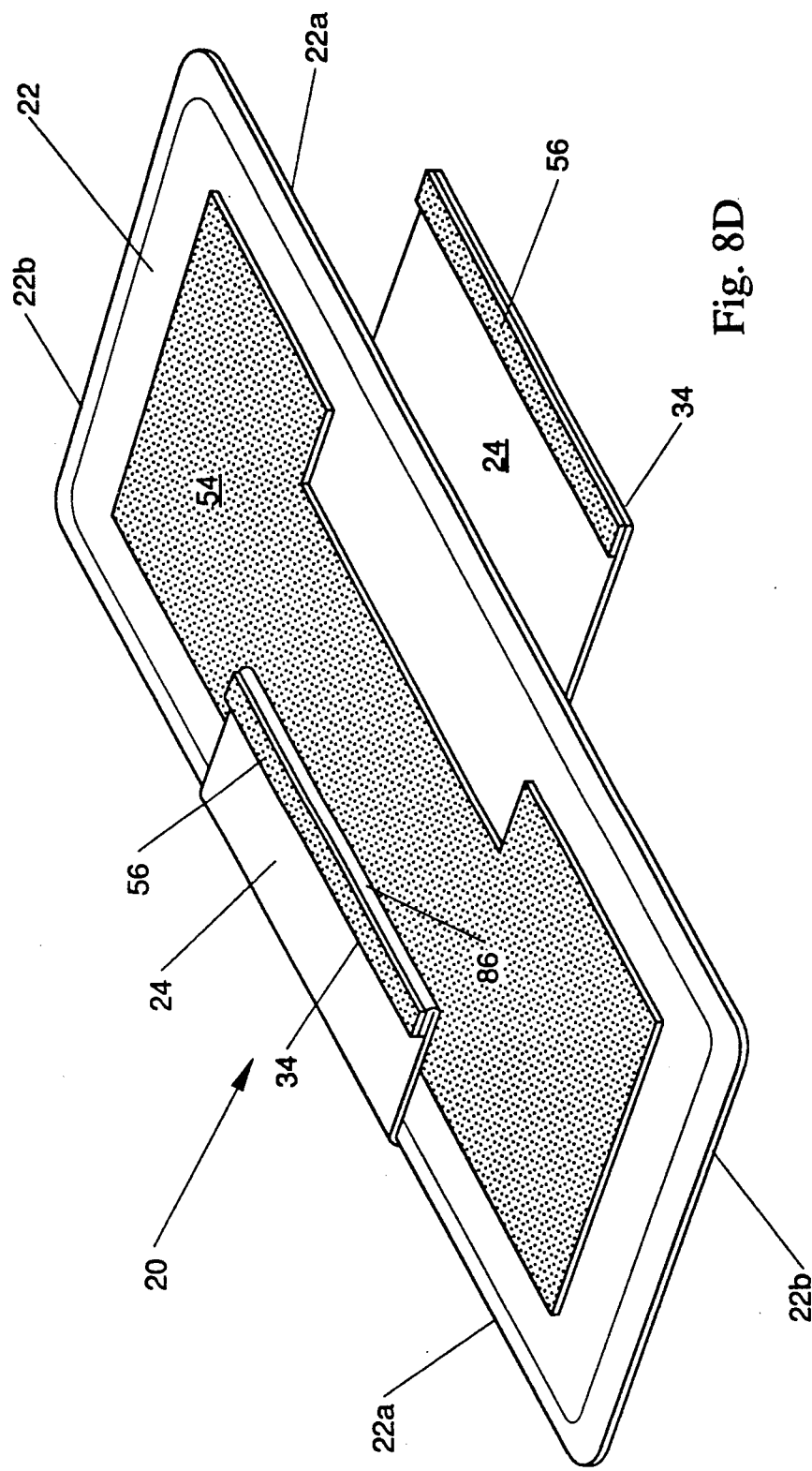
FIG. 8d is a perspective view of the sanitary napkin of FIG. 8c with one flap extended.

The sanitary napkin 20 is preferably made by assembling the main body portion 22 and flaps 24 as described herein before, folding the flaps over the garment side 22' of the main body portion 22 to form adhesive receiving portions 54' on the garment side 22' of the main body portion 22 and folding the portion of each flap 24 adjacent the distal edge 34 such that a portion of the garment side 24' of each flap 24 is facing outward to form an adhesive receiving portion 56', as shown in FIG. 8. A suitable adhesive is then applied to one side of a release liner 58 to form an adhesive patch 57 as shown in FIG. 8a. The release liner 58 is then applied to the sanitary napkin 20 such that the adhesive patch 57 of the release liner 58 is transferred to the adhesive receiving portion 56' of each flap 24 and the adhesive receiving portion 54' of the main body portion 22. This results in a sanitary napkin 20 having a single release liner 58 which covers both the central pad adhesive 54 and the flap adhesives 56, such as is shown in the partially cutaway perspective view of FIG. 8b. FIG. 8c shows the sanitary napkin 20 with the release liner 58 removed to show the flap adhesives 56 and the central pad adhesive 54 after the adhesive patch 57 is transferred from the release liner 58. FIG. 8d shows the sanitary napkin 20 of FIG. 8 with one of the flaps 24 extended.

Figure 9:
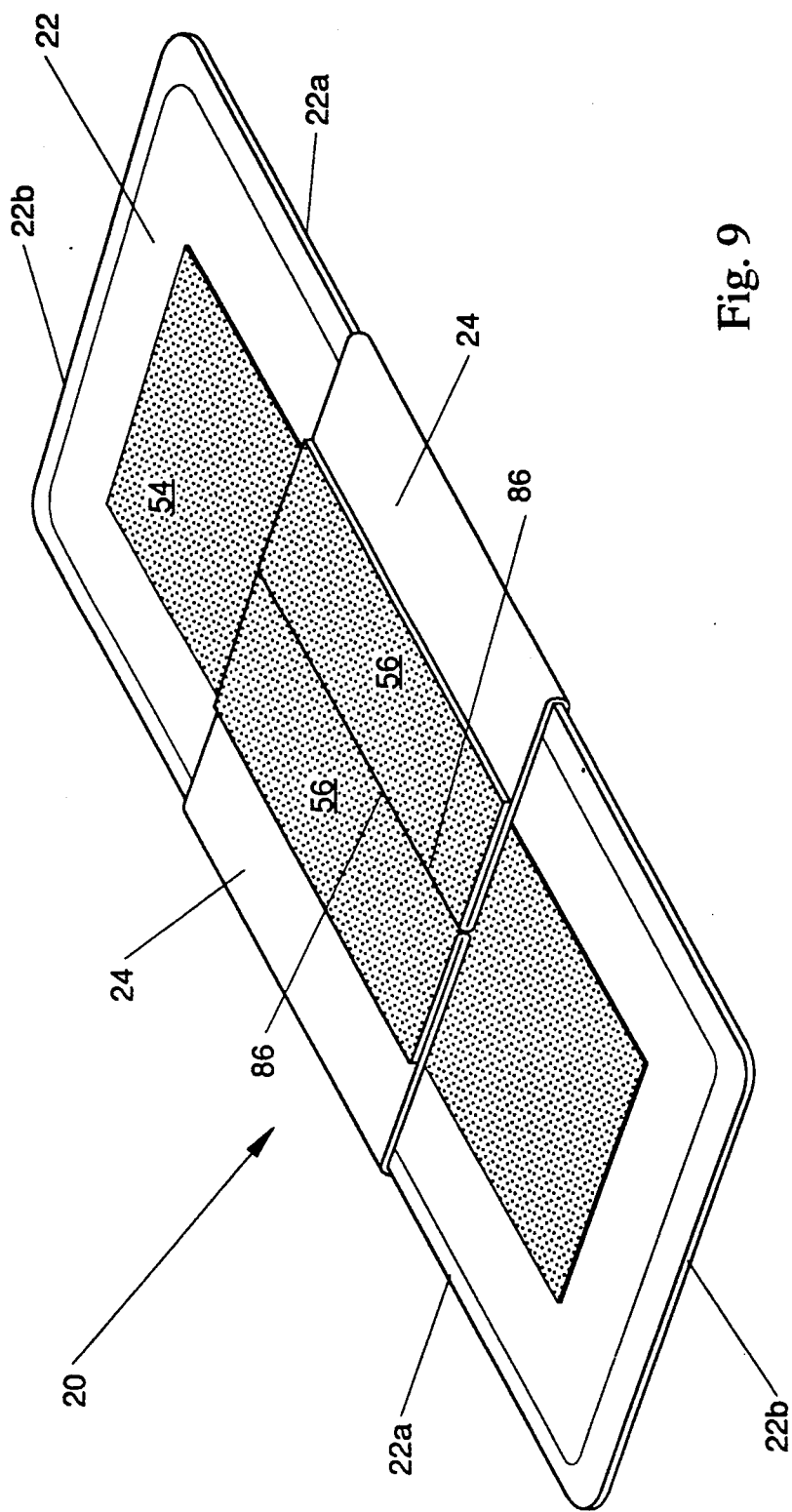
FIG. 9 is a perspective view of a sanitary napkin embodiment of the present invention having rectangularly shaped flaps which abut in the center of the main body portion.
Figure 9A:
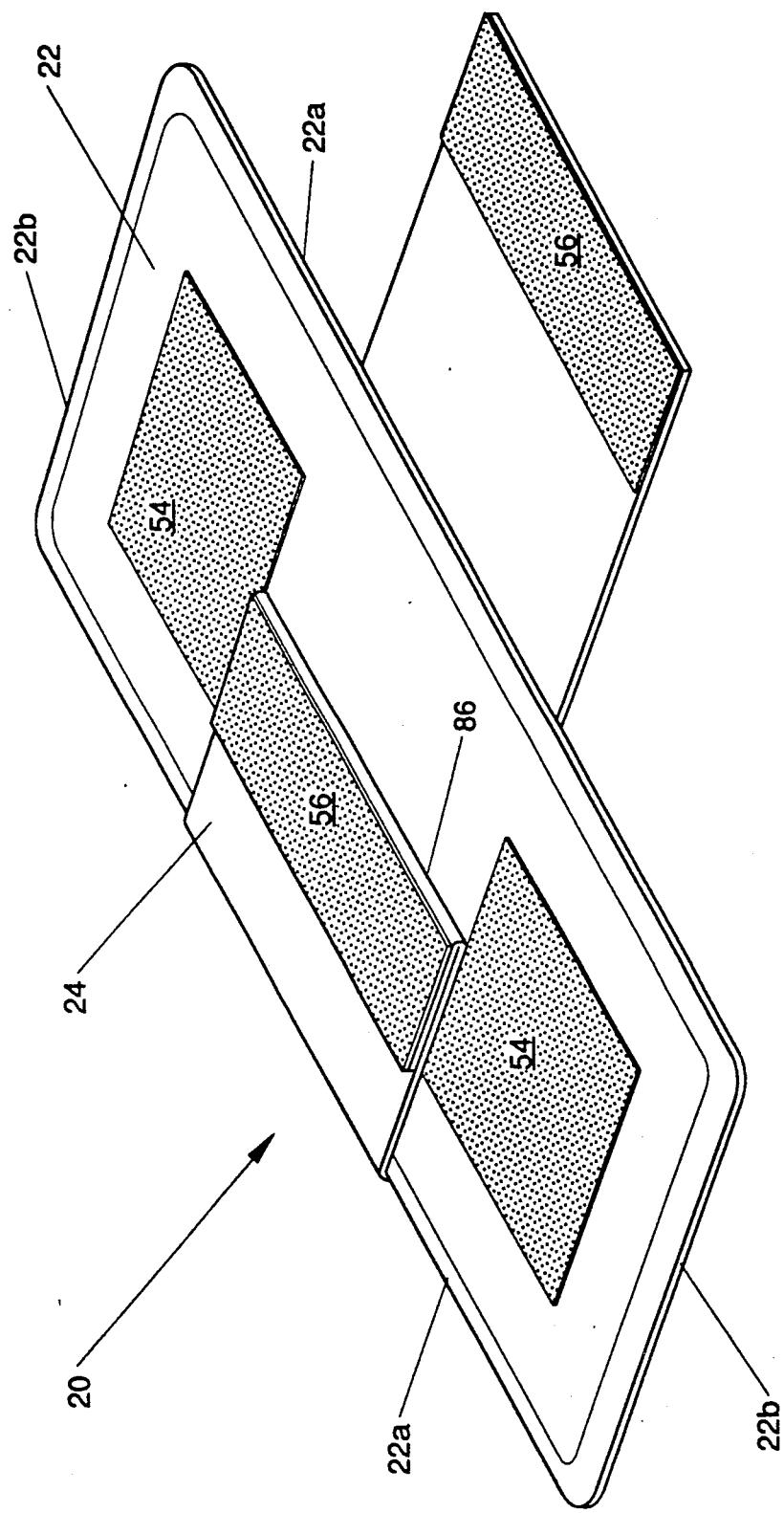
FIG. 9a is is a perspective view of the sanitary napkin of FIG. 9 with one of the flaps extended.

FIG. 9 shows an alternate sanitary napkin embodiment of the present invention with the release liner 58 removed to show the flap adhesives 56 and the central pad adhesive 54 after the adhesive patch 57 is transferred from the release liner 58. The sanitary napkin 20 of FIG. 9 comprises flaps 24 which abut at the fold lines 86. FIG. 9a shows the sanitary napkin 20 of FIG. 9 with one of the flaps 24 extended.

Figure 10:
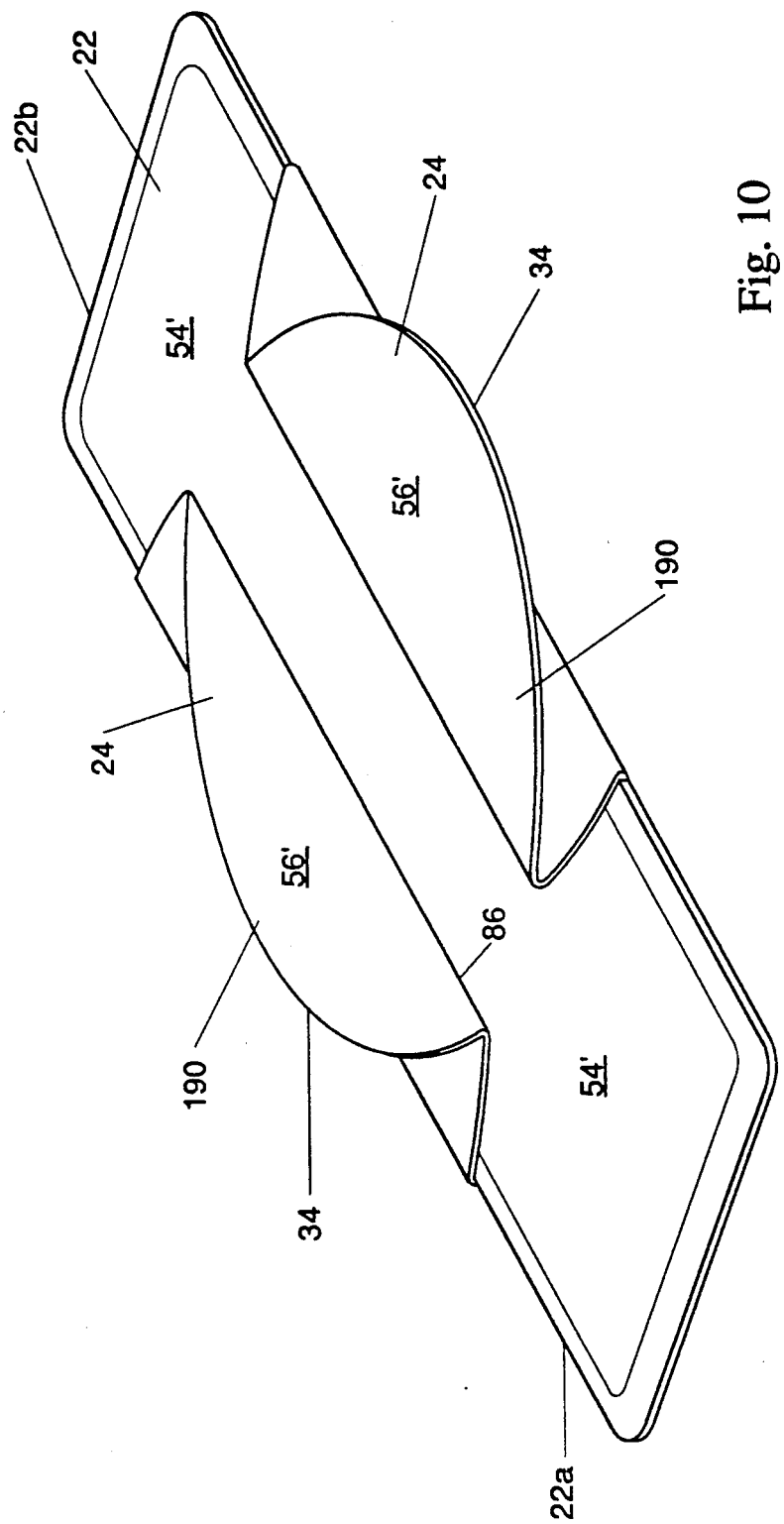
FIG. 10 is a perspective view of a sanitary napkin embodiment of the present invention prior to the adhesive being applied to the adhesive side of the sanitary napkin.
Figure 10A:
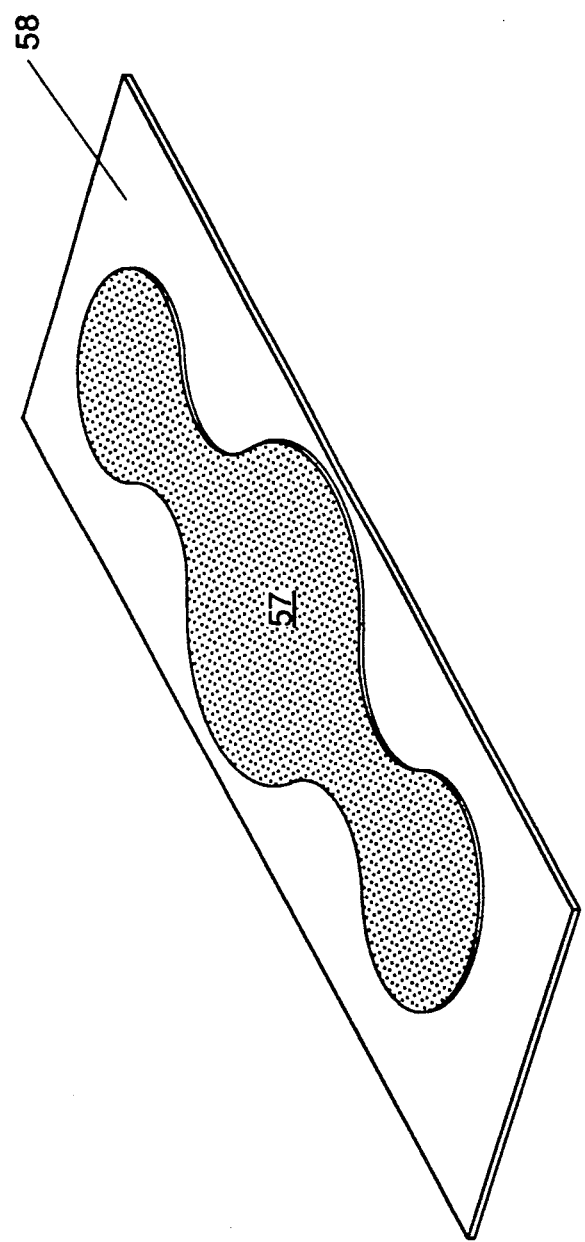
FIG. 10a is a perspective view of a release liner having a shaped adhesive patch removably secured thereto.
Figure 10B:
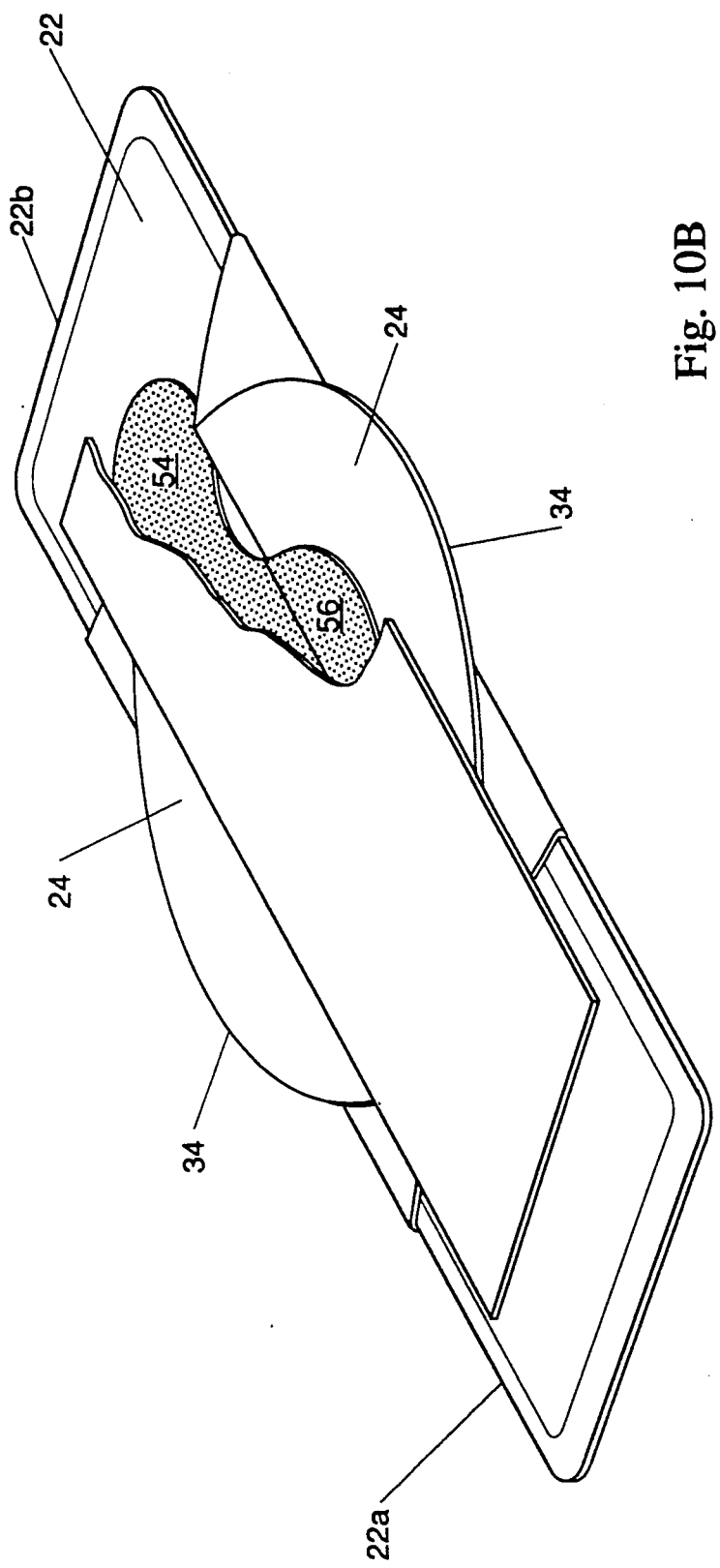
FIG. 10b is a perspective view of the sanitary napkin of FIG. 10 after the release liner and adhesive patch have been applied thereto, the release liner is partially cut-away to show the flap adhesive and the central pad adhesive.
Figure 10C:
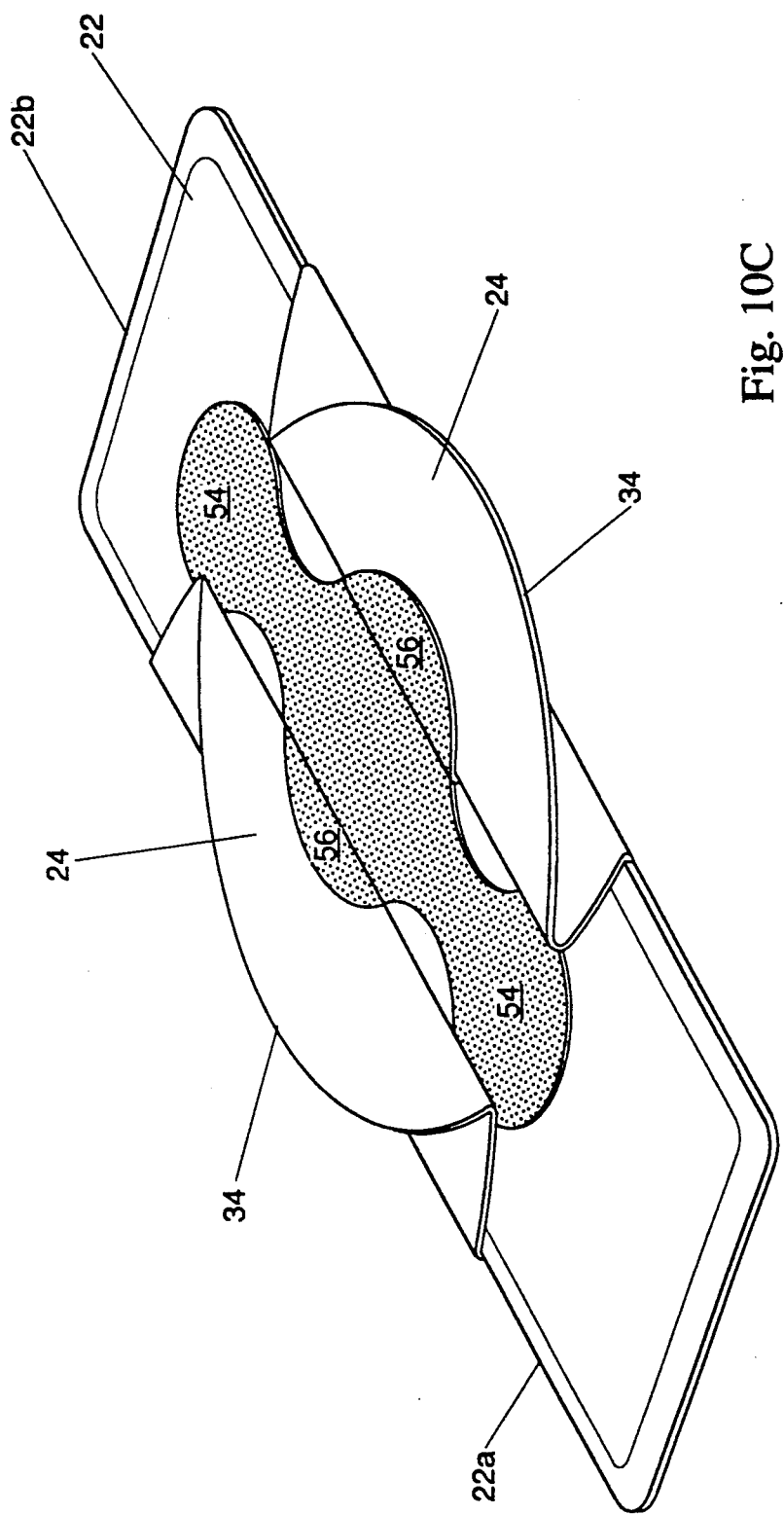
FIG. 10c is a perspective view of the sanitary napkin of FIG. 10b after the release liner has been removed.
Figure 10D:
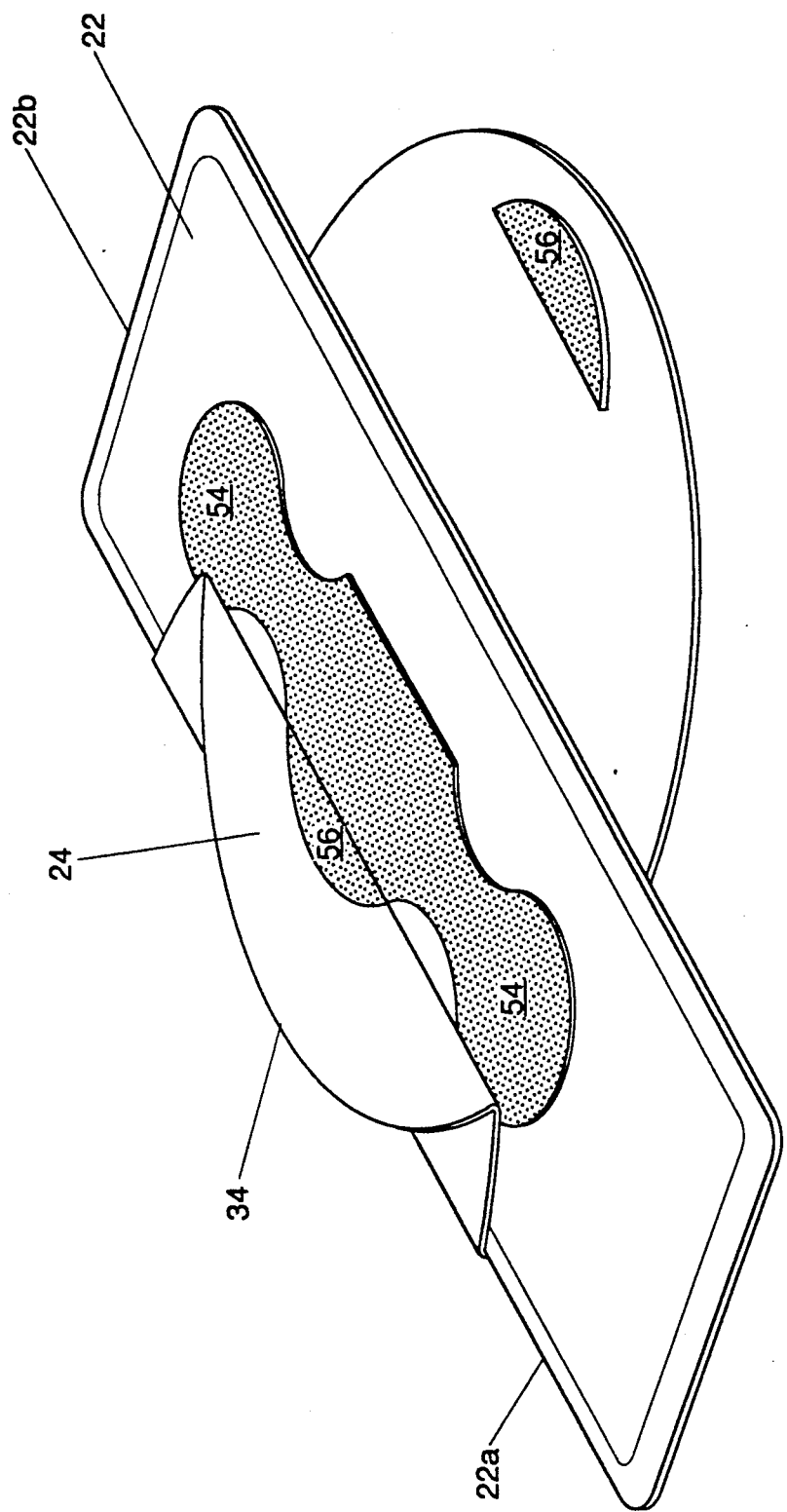
FIG. 10d is a perspective view of the sanitary napkin of FIG. 10c with one flap extended.

Although the flaps 24 and the adhesive patches 57 of the sanitary napkins 20 shown in FIGS. 8 and 9, are substantially rectangular in shape, it should be understood that this is only one possible configuration for the flaps 24 and adhesive patches 57. An alternate configuration is shown in FIG. 10. The sanitary napkin 20 of FIG. 10 comprises flaps 24 which are generally sinusoidal in shape and are folded to form adhesive receiving portions 54' on the garment side 22' of the main body portion 22 and adhesive receiving portions 56' on the garment side 24' of each flap 24. FIG. 10a shows a release liner 58 with an adhesive patch 57 which is also generally sinusoidal in shape. It can be seen in FIG. 10b that after the release liner 58 is applied to the sanitary napkin 20, portions of the adhesive patch 57 will be transferred from the release liner 58 to the adhesive receiving portions 56' of each flap 24 and the adhesive receiving portions 54' of the main body portion 22. FIG. 10c shows the sanitary napkin 20 with the release liner 58 removed. FIG. 10d shows the sanitary napkin 20 with one flap 24 extended.

Preferably, the distal edge 34 of each flap 24 extends beyond the periphery 23 of the main body portion 22. This configuration allows the distal edge 34 of the flap 24 to form a graspable tab member 190.

Preferably each flap 24 will be provided with a graspable tab member 190. As used herein, the term "graspable tab member" will refer to a portion, element or component of the flap 24 which extends beyond the periphery of the main body portion 22 when the sanitary napkin 20 is in a folded configuration. The graspable tab member 190 may be used to remove the flap 24 from the garment side 22' of the main body portion 22. The graspable tab member 190 preferably extends beyond the periphery 23 of the main body portion 22 at least about 2 millimeters to about 5 millimeters. More preferably, the tab member 90 extends beyond the periphery 23 of the main body portion 22 at least about 5 millimeters to about 10 millimeters. There are many different fold configurations which will result in the distal edge 34 of the flap 24 extending beyond the periphery 23 of the main body portion 22. An example of particularly preferred fold configurations which results in the distal edge of the flap 24 forming a tab member 90, are shown in FIG. 10-10c. Other suitable fold configurations will be readily apparent to those skilled in the art.

Figure 7:
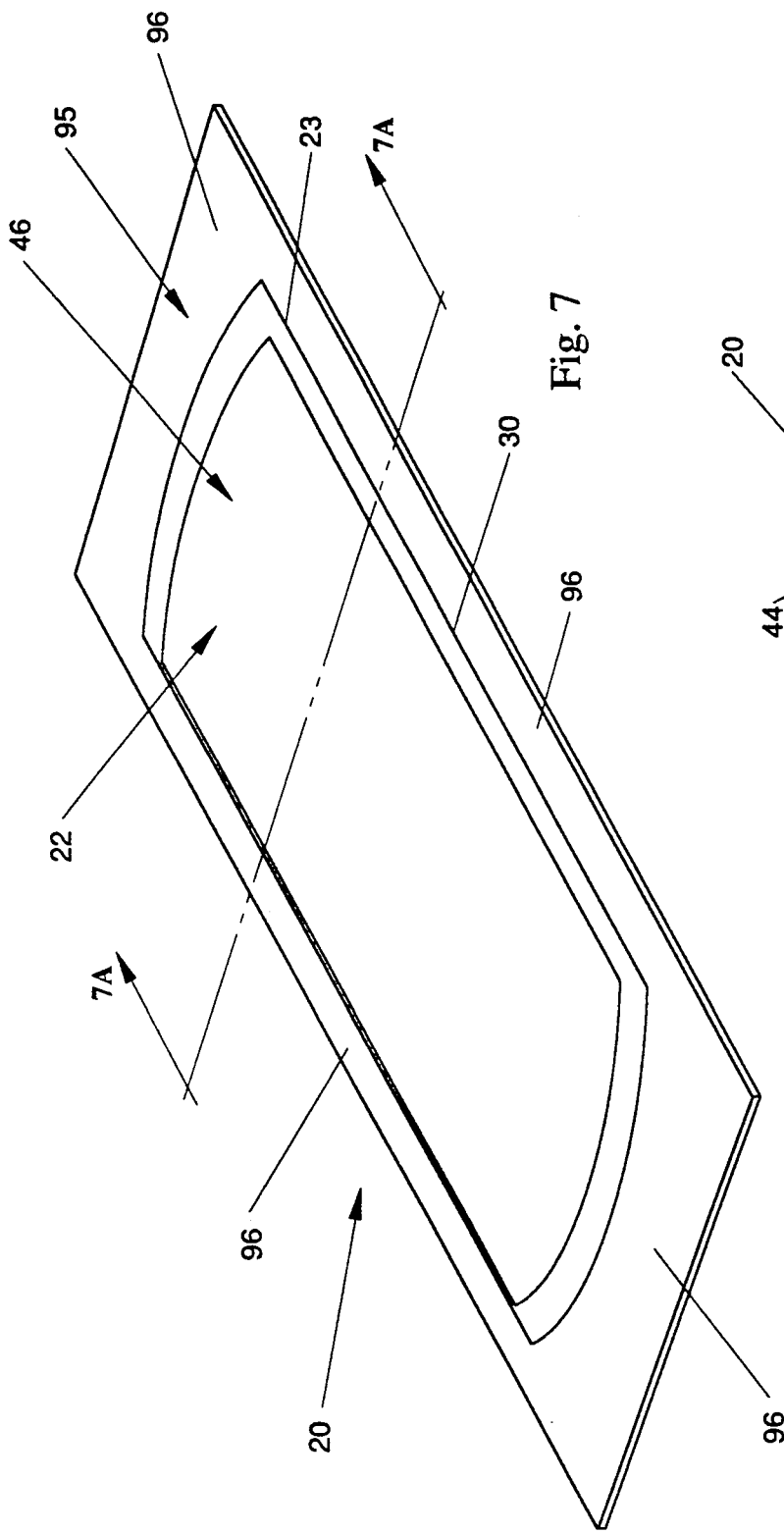
FIG. 7 is a perspective view of a sanitary napkin embodiment of the present invention and its associated wrapper prior to being folded and sealed.
Figure 7A:
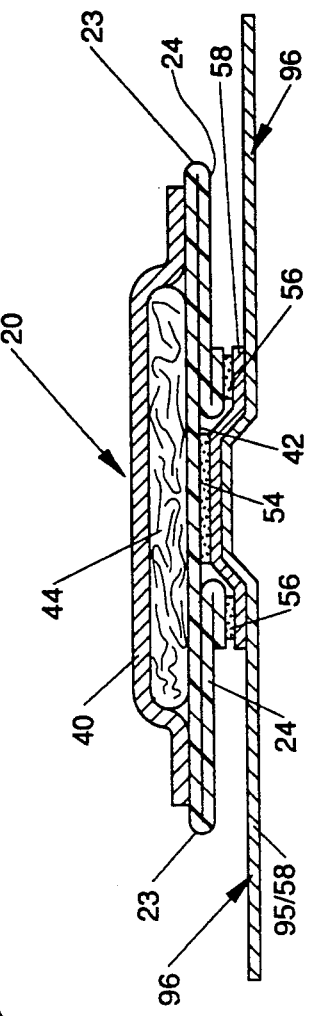
FIG. 7a is a cross sectional view of the sanitary napkin of FIG. 7 taken along section line 7A—7A.
Figures 7B, 7C:
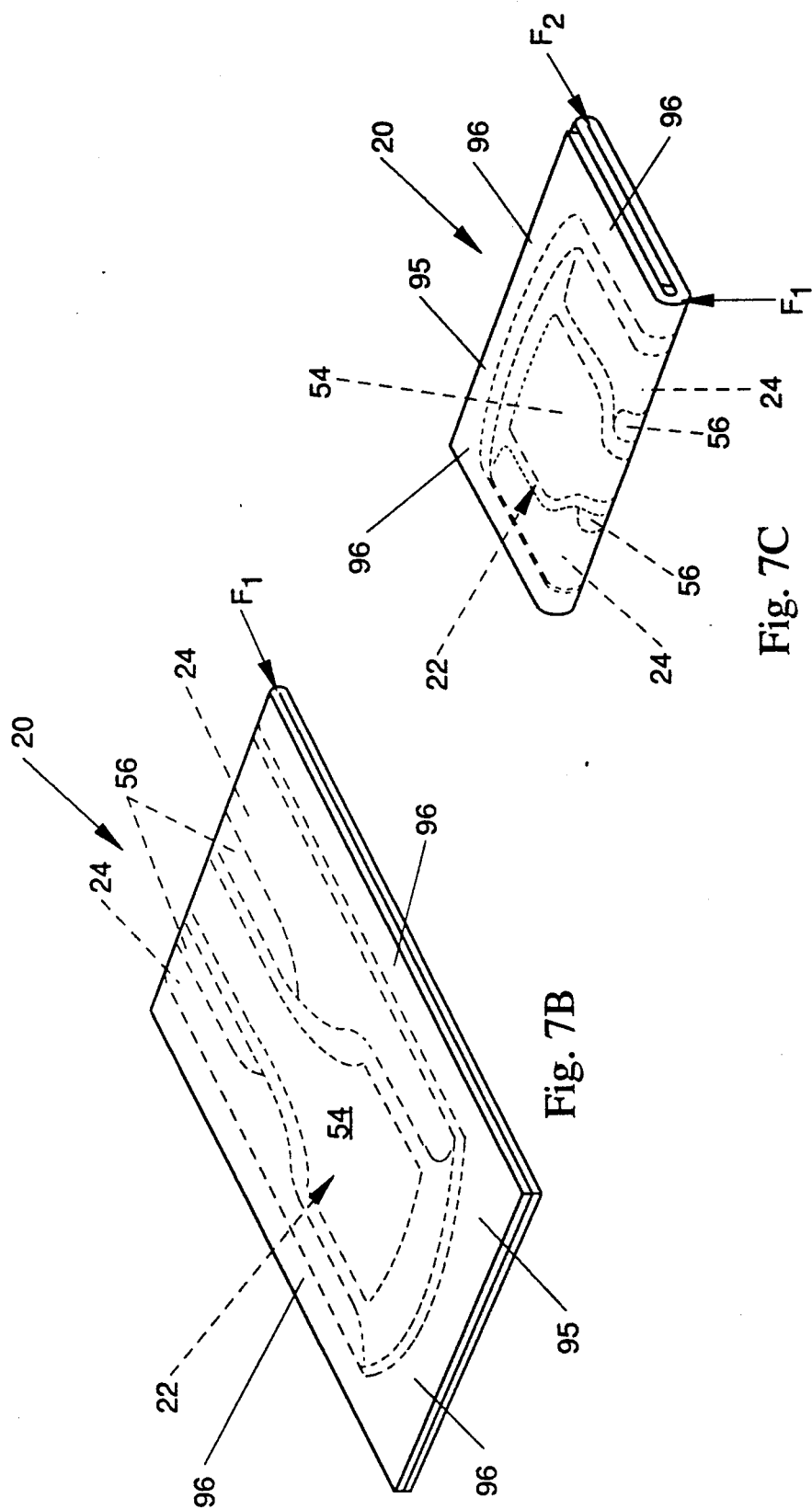
FIG. 7b is a perspective view of the sanitary napkin of FIG. 7 and its associated wrapper after they have been folded along a single fold line and sealed.
FIG. 7c is a perspective view of the sanitary napkin of FIG. 7 and its associated wrapper after they have been folded along two fold lines and sealed.

In a particularly preferred embodiment of the present invention, the sanitary napkin 20 will comprise a wrapper which overlays one major surface of the sanitary napkin and by folding the sanitary napkin and sealing the wrapper, an individually packaged disposable absorbent article can be provided. Such an embodiment is shown in FIG. 7. Referring to FIG. 7, it can be seen that the wrapper 95 is joined to the release liner 58. The wrapper 95 comprises edge portions 96 which extend beyond the periphery 23 of the absorbent assembly 46 of the main body portion 22. The sanitary napkin 22 with the wrapper 95 secured thereto, is folded about at least one fold-axis as shown in FIG. 7b such that the edge portions 96 of the wrapper 95 are overlapped. The edge portions 96 are then frangibly sealed together to form an individually packaged disposable sanitary napkin 20. Although the wrapper 95 and release liner 58 are shown as separate elements secured together, the wrapper 95 could be treated, e.g., treated with silicone, to function as the release liner 58.

Alternatively, the sanitary napkin with the wrapper 95 secured thereto can be folded along two or more fold-axes and then the edge portions 96 of the wrapper 95 may be frangibly sealed to form an individually packaged disposable sanitary napkin 20. FIG. 7c shows such a sanitary napkin folded along two fold axes F1 and F2. The release liner 58 may form the wrapper 95 as shown in FIG. 7a. Alternatively, the wrapper 95 may be a discrete piece of material joined to the release liner 58.

The edge portions 96 are frangibly sealed using any of the well-known sealing techniques. For example, the edge portions 96 may be heat sealed, glued, or ultrasonically bonded.

Individually packaged sanitary napkins (without the folded optional flaps 24 of the present invention) are disclosed in U.S. Pat. No. 4,556,146, entitled "Individually Packaged Disposable Absorbent Article", issued Dec. 3, 1985 in the name of Swanson, et al. This patent is incorporated herein by reference.

A transverse cross sectional view of an alternate sanitary napkin embodiment of the present invention is shown in FIG. 3. A portion of the flaps 24 of the sanitary napkin 20 are removably secured to a portion of the central pad adhesive 54 and the sanitary napkin 20 is thereby held in a folded configuration. The portion of the flap 24 which superposes the central pad adhesive 54 must be removably secured thereto. In a particularly preferred embodiment, each flap 24 will be provided with a unitary release material 80 which will superpose a portion of the central pad adhesive 54 and allow the flaps 24 to be easily removed. There are many different methods of providing the flaps 24 with a unitary release material 80. Disposable absorbent articles comprising unitary release materials (without the folded optional flaps of the present invention) are discussed in greater detail in commonly-owned, co-pending U.S. patent application Ser. No. 07/906,593, entitled "Absorbent Article Comprising A Unitary Release Material", filed Jun. 30, 1992, in the name of Bruce W. Lavash et al., which patent application is incorporated herein by reference. The unitary release material described therein could be utilized as the unitary release material 80 of the flaps 24 of the present invention.

In an alternate embodiment, the flaps of the sanitary napkin may have at least one zone of differential extensibility (or "zone of extensibility", or simply "zone") 50. Methods of providing zones of differential extensibility, are discussed in greater detail in commonly-assigned co-pending, U.S. patent application Ser. No. 07/769,891, "Absorbent Article Having Flaps and Zones of Differential Extensibility", filed Oct. 1, 1991, in the name of Bruce W. Lavash, et al., and in commonly-assigned, co-pending, U.S. patent application Ser. No. 07/832,246, "Absorbent Article Having Inwardly-Folded Pleated Flaps", filed Feb. 7, 1992, in the name of Kaoru Niihara and Thomas W. Osborn, III, which patent applications are incorporated herein by reference.

In an another alternative embodiment, the sanitary napkin 20 could be provided with an elastomer, such as an elastomeric strand, elastomeric ribbon, elastomeric film or the like. In such an embodiment the main body portion 22 would preferably comprise such an elastomer joined to at least a portion of each longitudinal edge 22a. A sanitary napkin comprising an elastomer is disclosed in U.S. patent application Ser. No. 07/811,348, "Elasticized Sanitary Napkin", filed Dec. 20, 1991, in the name of Diane Sneller, June Brennock, and Carl Bergman, which patent application is incorporated herein by reference.

D. Function of the Sanitary Napkin and The Optional Flaps With Relation To A Wearer's Undergarment The function of the sanitary napkin of the present invention will now be described in greater detail with relation to the wearer's undergarments.

Figure 4:
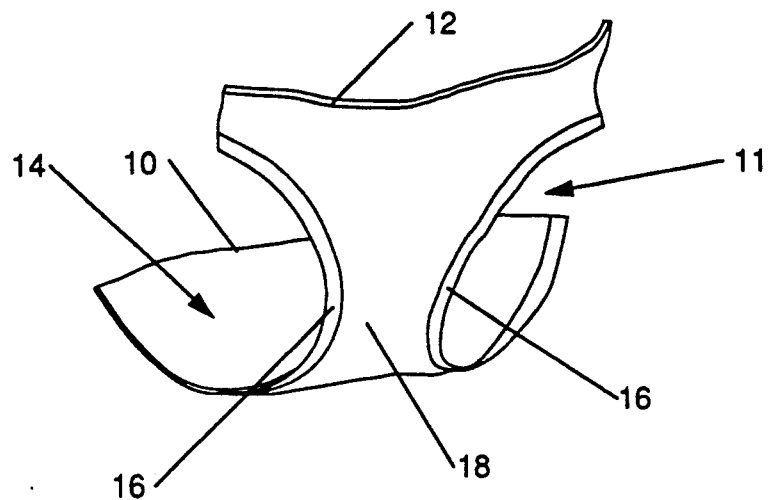
FIG. 4 is a perspective view of the crotch portion of a women's panties.

FIG. 4 is a depiction of the crotch portion 14 of an undergarment 11 of the type commonly worn by many women and well known as a panty. A panty 11 comprises a front section 10, a back section 12, and a crotch portion 14 which joins the front and back sections. The crotch portion 14 comprises two side edges 16 and center crotch portion 18.

Figure 6:
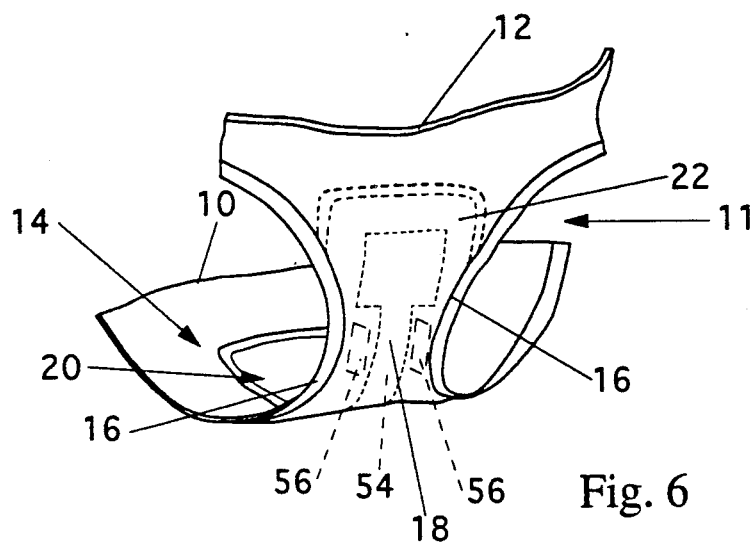
FIG. 6 is the same perspective view of the women's panties shown in FIG. 4 with the a sanitary napkin embodiment of the present invention having the flaps in the folded configuration, being placed therein for use.

The sanitary napkin 20 of the present invention may be utilized by removing the release liner 58 from the securement members and placing the sanitary napkin 20 in a panty 11 as shown in FIG. 6. The center of main body portion 22 is placed in crotch portion 14 of the panty with one end of main body portion 22 extending towards the front section 10 of the panty and the other end towards the back section 12. The backsheet 42 is placed in contact with the inner surface of center crotch portion 18 of the panty. The flaps 24 remain in their folded configuration, and the face 87 of the flap adhesives 56 are secured to the undergarment. Central pad adhesive 54 and flap adhesive 56 maintain main body portion 22 in position. The panty is pulled up into position on the wearer's lower torso. Although, the flaps 24 have not been used and remain in their folded configuration, the flaps adhesives 56 will assist in maintaining the main body portion 22 in position in the central crotch portion 18.

Figure 5:
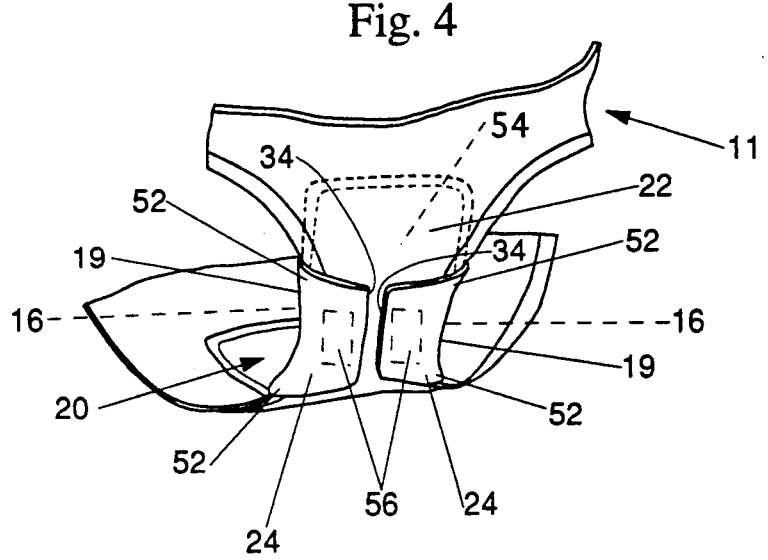
FIG. 5 is the same perspective view of the women's panties shown in FIG. 4 with the sanitary napkin embodiment of the present invention being placed therein for use with the flaps extended and affixed to the underside of the panties.

Alternatively, the sanitary napkin 20 of the present invention may be utilized by removing the release liner 58 from the securement members and placing the sanitary napkin 20 in a panty 11 as shown in FIG. 5. The center of main body portion 22 is placed in crotch portion 14 of the panty with one end of main body portion 22 extending towards the front section 10 of the panty and the other end towards the back section 12. The backsheet 42 is placed in contact with the inner surface of center crotch portion 18 of the panty. Central pad adhesive 54 maintains main body portion 22 in position. Each of the flaps 24 is removed from between the panty 11 and the main body portion 22, the distal edges 34 of flaps 24 are folded around the side edges 16 of the panty, and the flap adhesives 56 are secured to the underside of the panty.

Thus, the present invention provides a sanitary napkin having flap adhesives and a central pad adhesive which can be covered by one side of a single release liner.

While particular embodiments of the present invention have been illustrated and described, it would be obvious to those skilled in the art that various other changes and modifications can be made without departing from the spirit and scope of the invention.

What is claimed is:

1. An absorbent article in a folded configuration having an adhesive side and a non-adhesive side, said absorbent article comprising:
    a main body portion comprising an absorbent assembly, a body-facing side, a garment side, and a periphery comprising longitudinal edges and transverse edges; and
    a pair of flaps, each of said flaps being joined along a line of juncture to said main body portion, and each flap comprising a proximal edge adjacent to the line of juncture, a distal edge disposed away from the line of juncture, a body-facing side, and a garment side, each said flap being folded to be over the garment side of said main body portion to form a first flap portion and each said flap being folded again to form a second flap portion having a body-facing side and a garment side, said garment side of said second flap portion facing away from said garment side of main body portion such that, in the absorbent article's folded configuration, said garment side of said main body portion and said garment side of each said second flap portion all face opposite said body-facing side of said main body portion, and
    a flap securement member joined to said garment side of said second flap portion of each said flap whereby at least a portion of said flap securement member on said second flap portion overlays said main body portion such that each said flap securement member forms at least a portion of said adhesive side of the absorbent article.

2. The absorbent article of claim 1 wherein said flap securement member comprises a pressure sensitive adhesive.

3. The absorbent article of claim 1 wherein said flap securement member comprises a mechanical fastening material.

4. The absorbent article of claim 2 additionally comprising at least one pad securement member joined to the garment side of said main body portion.

5. The absorbent article of claim 4 wherein said pad securement member comprises a pressure sensitive adhesive.

6. The absorbent article of claim 4 wherein said pad securement member comprises a mechanical fastening material.

7. The absorbent article of claim 2 additionally comprising a protective release liner which superposes each said flap securement member.

8. The absorbent article of claim 7 additionally comprising an outer wrapper joined to said protective release liner, said outer wrapper comprising longitudinal edge portions which extend beyond the periphery of said main body portion, said absorbent article and said protective release liner being folded as a unit about at least one fold-axis and said longitudinal edge portions being frangibly sealed.

9. The absorbent article of claim 8 wherein said absorbent article and said protective release liner are folded as a unit about two fold-axes and said longitudinal edge portions are frangibly sealed.

10. The absorbent article of claim 2 wherein said distal edge of each said flaps extends beyond the longitudinal edge of said main body portion to form a graspable tab member.

11. The absorbent article of claim 4 wherein said pad securement member forms securement regions and non-securement regions on the garment side of said main body portion.

12. The absorbent article of claim 11 wherein each of said flaps superposes a non-securement region of the main body portion.

13. The absorbent article of claim 11 wherein at least a portion of each of said flaps is releasably secured to a securement region of the main body portion.

14. A method of using an absorbent article, the method comprising the steps of:
    providing the absorbent article of claim 5;
    providing an undergarment comprising a front section; a back section; and a crotch portion which joins said front section and said back section, said crotch portion comprising two side edges, a center crotch portion, an inside, and an underside;
    removing said wrapper comprising said release strip or removing said release strip;
    releasing said flaps from said main body portion,
    extending said flaps from their folded configuration;

positioning said absorbent article on said inside of said crotch portion of said undergarment such that said main body portion is positioned in said center crotch portion with one end of said main body portion extending toward said front section and the other end of said main body portion extending toward back section;

securing said pad securement member to said inside of said crotch portion of said undergarment, such that said pad securement member maintains said main body portion of said absorbent article in said center crotch portion of said undergarment;

wrapping each of said flaps around said side edges of said undergarment; and securing said flap securement member of each of said flaps to said underside of said crotch portion of said undergarment.

15. A method for making an absorbent article in a folded configuration comprising an adhesive side, a non-adhesive side and flaps with flap adhesives which form at least a portion of the adhesive side of said absorbent article, the method comprising the steps of:

(a) providing an absorbent article comprising a garment side, a body-facing side, a main body portion, and a pair of flaps joined to said main body portion along a line of juncture, said main body portion comprising an absorbent assembly, each of said flaps comprising a proximal edge adjacent the line of juncture, a distal edge disposed away from the line of juncture;

(b) folding each said flap over said garment side of said absorbent article, (c) folding each flap a second time such that a portion of the garment side of each of said flaps overlays and faces away from the garment side of said main body portion to form an adhesive receiving portion on each of said flaps;

(d) Applying an adhesive to at least said adhesive receiving portions of each of said flaps to form flap securement members;

(e) providing a wrapper comprising a release strip overlaying the adhesive portions of each said second flap portions and at least a portion of the adhesive side of the main body portion.

16. The method of claim 15 wherein the step of applying said adhesive to at least said adhesive receiving portion of each of said flaps, additionally comprises applying adhesive to a portion of the garment side of the main body portion to form a pad securement member.

17. The method of claim 16 wherein the step of applying said adhesive to said adhesive receiving portion of each of said flaps and applying adhesive to said garment side of said main body portion, comprises printing said adhesive onto said adhesive receiving portion of each of said flaps and onto said garment side of said main body portion.

* * * * *

UNITED STATES PATENT AND TRADEMARK OFFICE
CERTIFICATE OF CORRECTION

PATENT NO. : 5,330,461
DATED : July 19, 1994
INVENTOR(S) : Karen K. Leeker

It is certified that error appears in the above-identified patent and that said Letters Patent is hereby corrected as shown below:

Column 1, line 42    delete "parities" and insert --panties--.

Signed and Sealed this

Second Day of March, 1999

Attest:

Q. TODD DICKINSON

*Attesting Officer*    Acting Commissioner of Patents and Trademarks